(12) United States Patent
Ritter et al.

(10) Patent No.: US 8,753,853 B2
(45) Date of Patent: Jun. 17, 2014

(54) PROCESS FOR MAKING LINEAR DICARBOXYLIC ACIDS FROM RENEWABLE RESOURCES

(75) Inventors: Joachim C. Ritter, Wilmington, DE (US); Sourav Kumar Sengupta, Wilmington, DE (US); Hasan Dindi, Wilmington, DE (US); Robert D. Fallon, Elkton, MD (US); Ekaterini Korovessi, Wilmington, DE (US); Andrew C. Eliot, Wilmington, DE (US); John Joseph Hagedorn, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 266 days.

(21) Appl. No.: 13/131,138

(22) PCT Filed: Dec. 11, 2009

(86) PCT No.: PCT/US2009/067729
§ 371 (c)(1),
(2), (4) Date: Aug. 19, 2011

(87) PCT Pub. No.: WO2010/068904
PCT Pub. Date: Jun. 17, 2010

(65) Prior Publication Data
US 2011/0300594 A1    Dec. 8, 2011

Related U.S. Application Data

(60) Provisional application No. 61/122,074, filed on Dec. 12, 2008.

(51) Int. Cl.
*C12P 7/44* (2006.01)

(52) U.S. Cl.
USPC ............................ 435/142; 435/145; 435/162

(58) Field of Classification Search
USPC .......................................... 435/142, 145, 162
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,855,231 A | 8/1989 | Stroman et al. | |
| 4,992,605 A | 2/1991 | Craig et al. | |
| 5,231,020 A | 7/1993 | Jorgensen et al. | |
| 5,254,466 A | 10/1993 | Picataggio et al. | |
| 5,620,878 A | 4/1997 | Picataggio et al. | |
| 5,648,247 A | 7/1997 | Picataggio et al. | |
| 5,705,722 A | 1/1998 | Monnier et al. | |
| 6,123,835 A | 9/2000 | Ackerson et al. | |
| 6,288,275 B1 | 9/2001 | Turner | |
| 6,428,686 B1 | 8/2002 | Ackerson et al. | |
| 6,881,326 B2 | 4/2005 | Ackerson et al. | |
| 7,291,257 B2 | 11/2007 | Ackerson et al. | |
| 8,119,847 B2 * | 2/2012 | Dindi et al. ................... | 585/240 |
| 2004/0146999 A1 | 7/2004 | Fallon et al. | |
| 2005/0181491 A1 | 8/2005 | Eirich et al. | |
| 2006/0207166 A1 | 9/2006 | Herskowitz et al. | |
| 2007/0260102 A1 | 11/2007 | Duarte Santiago et al. | |
| 2008/0071125 A1 | 3/2008 | Li | |

FOREIGN PATENT DOCUMENTS

| | | | |
|---|---|---|---|
| EP | 1273663 A2 | 7/1998 | |
| JP | 2003171670 A | * | 6/2003 |
| WO | 00/20620 A1 | 4/2000 | |
| WO | WO 2007077568 A1 | * | 7/2007 |
| WO | 2007/003708 A1 | 11/2007 | |
| WO | 2008/020048 A2 | 2/2008 | |
| WO | 2008/020048 A3 | 2/2008 | |

OTHER PUBLICATIONS

Mizukami, et al. JP 2003-171670. Machine Translated on Apr. 19, 2013 from the JPO Website.*
Barbiroli, Giancarlo et al. Aliphatic Polyesters of Dodecanedioic acid: Synthesis and Properties. European Polymer Journal 39. 2003. pp. 655-661.*
Murzin et al Industrial Engineering Chemical Research, vol. 45, (2006) pp. 5708-5715.
Kenneth D. Green et al, "Candida cloacae oxidation of long-chain fatty acids to dioic acids", Enzyme and Microbial Technology, 27, (2000), 205-211.
Ooi Yean Sang, "Biofuel production from catalytic cracking of palm oil", Energy Sources (2003), 25(9), 859-869.
Chinese Patent Abstract No. 1570124A, dated Jan. 26, 2005 by Yongjun Qiu.
Chinese Patent Abstract No. 1502700A, dated Jun. 9, 2004 by Yuantong Chen et al.

* cited by examiner

*Primary Examiner* — Susan Hanley
*Assistant Examiner* — Nghi Nguyen

(57) ABSTRACT

This invention provides a process of making a linear dicarboxylic acid of $C_{10}$, $C_{12}$, $C_{14}$, $C_{16}$ or $C_{18}$ chain length, the process comprising providing a feed which is a renewable resource, contacting the feed with a catalyst in the presence of hydrogen and at a temperature of about 250° C. to about 425° C. and at a pressure of about 500 psig to about 2500 psig (3450 kPa to about 17,250 kPa) to produce a hydrocarbon product having at least a 5:1 ratio of even-numbered alkanes to odd-numbered alkanes and comprising a linear alkane of $C_n$ chain length; and fermenting at least a portion of the linear alkane of $C_n$ chain length to a linear dicarboxylic acid of $C_n$ chain length, wherein n=10, 12, 14, 16 or 18. The catalyst comprises an oxide, molybdenum, and one or more active metals selected from the group consisting of nickel, cobalt, and mixtures thereof and the catalyst is in sulfided form.

18 Claims, No Drawings

PROCESS FOR MAKING LINEAR DICARBOXYLIC ACIDS FROM RENEWABLE RESOURCES

This application claims priority under 35 U.S.C. §119(e) from, and claims the benefit of, U.S. Provisional Application No. 61/122,074, filed Dec. 12, 2008, which is by this reference incorporated in its entirety as a part hereof for all purposes.

TECHNICAL FIELD

The present invention relates to a process for the production of linear dicarboxylic acids.

BACKGROUND

Carboxylic acids, particularly long chain dicarboxylic acids, are commercially important products utilized in the production of polymers, adhesives, perfumes, and antibiotics. Aliphatic dicarboxylic acids of the form $HO(O)C(CH_2)_mC(O)OH$, where m=7 to 16, are used as polymer intermediates, for example as comonomers in nylon or polyester products. While chemical routes for the synthesis of long chain linear dicarboxylic acids from petrochemical feedstocks are available, the synthesis is complicated and results in mixtures containing dicarboxylic acids of shorter chain lengths. As a result, extensive purification steps are necessary to obtain the dicarboxylic acids in the purity required for polymer uses. Production of dicarboxylic acids can also occur by fermentation with various microorganisms, e.g. yeast, using alkanes or fatty acids as the carbon source. The alkanes or fatty acids can be obtained from petroleum feedstocks.

The high cost and increased environmental footprint of fossil fuels and limited petroleum reserves in the world have increased the interest in renewable fuel sources. Renewable resources include ethanol from corn and sugar for use in automobiles, and plant oils for use as diesel fuel. Research in the diesel fuel area includes two main areas, bio-diesel and green diesel.

The demand for renewable bio-based polymers having similar or better performance characteristics than petrochemical-based polymers, together with increasing fossil raw material prices, make it highly desirable to develop a process for the production of linear, long chain dicarboxylic acids from renewable feedstock. Furthermore, an economical bio-based process for the production of linear, long chain dicarboxylic acids which minimizes waste and maximizes productive use of the renewable feedstock is desired.

SUMMARY

This invention involves a process for the production of linear dicarboxylic acids from renewable resources. Linear hydrocarbons of $C_{10}$, $C_{12}$, $C_{14}$, $C_{16}$ or $C_{18}$ chain length, obtained by hydrotreatment of fatty acids or fatty acid esters, are fermented to linear dicarboxylic acids of the same carbon chain length as the hydrocarbon. The remaining hydrocarbons may be used as diesel fuels or in the production of diesel fuels.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One alternative embodiment hereof involves the production from renewable resources of a linear dicarboxylic acid of $C_{10}$, $C_{12}$, $C_{14}$, $C_{16}$ or $C_{18}$ chain length. A feed which is a renewable resource is contacted with a catalyst under hydrotreating reaction conditions to produce a hydrocarbon product having at least a 5:1 ratio of even-numbered hydrocarbons to odd-numbered hydrocarbons and comprising a linear hydrocarbon of $C_{10}$, $C_{12}$, $C_{14}$, $C_{16}$ or $C_{18}$ chain length. The linear hydrocarbon having the carbon chain length of the desired diacid product is then fermented to the linear dicarboxylic acid of the corresponding carbon chain length. The residual hydrocarbon product can be used as diesel fuel or as an additive to blend with petro diesel. Examples of appropriate feeds include but are not limited to fatty acids, esters of fatty acids derived from triglycerides, vegetable oils, and animal oils. The catalyst comprises an oxide, molybdenum, and one or more active metals selected from the group consisting of nickel, cobalt, and mixtures thereof.

In one of the alternative embodiments of this invention, a process is provided that includes:
(a) providing a feed which is a renewable resource;
(b) contacting the feed with a catalyst in the presence of hydrogen to produce a hydrocarbon product having at least a 5:1 ratio of even-numbered alkanes to odd-numbered alkanes and comprising a linear alkane of $C_n$ chain length; and
(c) fermenting at least a portion of the linear alkane of $C_n$ chain length to a linear dicarboxylic acid of $C_n$ chain length;
wherein n=10, 12, 14, 16 or 18; and the catalyst comprises an oxide, molybdenum, and one or more active metals selected from the group consisting of nickel, cobalt, and mixtures thereof; and the catalyst is in sulfided form.

In another alternative embodiment of the processes provided by this invention, the feed may be contacted with a catalyst in the presence of hydrogen and at a temperature of about 250° C. to about 425° C. and at a pressure of about 500 psig to about 2500 psig (3450 kPa to about 17,250 kPa).

In another alternative embodiment of the processes provided by this invention, the feed is
(a) an oil derived from plants and/or animals and comprising one or more free fatty acids and/or one or more triglycerides, the oil comprising at least about 5 mole % of a linear fatty acid of $C_n$ chain length, and/or at least about 5 mole % of a triglyceride derived from a linear fatty acid of $C_n$ chain length;
(b) an alkyl ester of a fatty acid derived from triglycerides, the ester comprising at least about 5 mole % of an ester of a linear fatty acid of $C_n$ chain length; or
(c) a mixture thereof.

In a further alternative embodiment of the processes provided by this invention, the feed is an oil comprising at least about 5 mole % of a linear fatty acid of $C_n$ chain length. In one embodiment, the fatty acid is selected from the group consisting of lauric acid, myristic acid, palmitic acid, or a combination of these. In another embodiment, the feed is a vegetable oil selected from the group consisting of coconut oil, palm kernel oil, palm oil, rapeseed oil, canola oil, soybean oil, cottonseed oil, or a combination of these. In another embodiment, the feed comprises poultry fat, yellow grease, tallow, or a combination of these. In another embodiment, the feed is an ester of a fatty acid derived from triglycerides, the ester comprising at least about 5 mole % of an ester of a linear fatty acid of $C_n$ chain length. In another embodiment, the ester is a methyl ester. In another embodiment of the process, the feed is a renewable resource obtained from a bio-diesel or green diesel process.

In yet another alternative embodiment of the processes provided herein, the hydrocarbon product has at least a 10:1 ratio of even-numbered alkanes to odd-numbered alkanes. In another embodiment, n=12, 14 or 16. In another embodiment, the temperature is about 275° C. to about 400° C. In another embodiment, the temperature is about 300° C. to about 375° C. In another embodiment, the pressure is about 1000 psig to about 2000 psig (about 7000 kPa to about 13,900 kPa). In another embodiment, the concentration of metal in the catalyst is 0.1 to 90 percent by weight, based on the total weight of the catalyst. In another embodiment, the concentration of metal in the catalyst is 0.5 to 60 weight percent.

In yet another alternative embodiment, the processes provided herein also include separating at least a portion of a linear alkane of $C_n$ chain length from the hydrocarbon product and using at least a portion of the residual hydrocarbon product as fuel. In another embodiment, n=10. In another embodiment, n=12. In another embodiment, n=14. In another embodiment, n=16. In another embodiment, n=18. In another alternative embodiment of the processes provided herein, a transformed *Candida maltosa* strain SW81/82 identified as ATCC 74431 is used in the fermentation. In another embodiment, a transformed *Candida maltosa* strain SW84/87.2 identified as ATCC 74430 is used in the fermentation. In another embodiment, a transformed *Pichia pastoris* strain SW64/65 identified as ATCC 74409 is used in the fermentation. In another embodiment of the process, n=12, 14 or 16.

The inventions disclosed herein include processes for the preparation of a dicarboxylic acid, processes for the preparation of products into which a dicarboxylic acid can be converted, the use of such processes, and the products obtained and obtainable by such processes.

Thus, in yet another alternative embodiment, the processes provided herein also include a step of polymerization to prepare a polymer, such as a nylon or polyester, from a dicarboxylic acid as provided herein.

It has been found herein that, to enable the advantageous fermentation of linear, long chain alkanes to dicarboxylic acids, it is desirable to produce linear alkanes in high purity without relying on the use of extractive separation methods to remove the branched alkane isomers.

Sequence Descriptions

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 represents the nucleotide sequence for the *Candida maltosa* cytochrome P450 monooxygenase Alk1-A gene.

SEQ ID NO:2 represents the nucleotide sequence for the *Candida maltosa* cytochrome P450 monooxygenase Alk2-A gene.

SEQ ID NO:3 represents the nucleotide sequence for the *Candida maltosa* cytochrome P450 monooxygenase Alk3-A gene.

SEQ ID NO:4 represents the nucleotide sequence for the *Candida maltosa* cytochrome P450 monooxygenase Alk4-A gene.

SEQ ID NO:5 represents the nucleotide sequence for the *Candida maltosa* cytochrome P450 monooxygenase Alk5-A gene.

SEQ ID NO:6 represents the nucleotide sequence for the *Candida maltosa* cytochrome P450 monooxygenase Alk6-A gene.

SEQ ID NO:7 represents the nucleotide sequence for the *Candida maltosa* cytochrome P450 monooxygenase Alk7 gene.

SEQ ID NO:8 represents the nucleotide sequence for the *Candida maltosa* cytochrome P450 monooxygenase Alk8 gene.

SEQ ID NO:9 represents the nucleotide sequence for the *Candida maltosa* cytochrome P450 reductase gene.

DETAILED DESCRIPTION

In the description of the subject matter of this application, the following definitional structure is provided for certain terminology as employed variously in the specification:

As used herein, the term "hydrocarbon" refers to a chemical compound consisting only of carbon and hydrogen atoms.

As used herein, the term "alkane" refers to a saturated hydrocarbon, a chemical compound consisting only of carbon and hydrogen atoms and containing exclusively single bonds.

As used herein, the term "paraffin" refers to linear (normal) alkanes.

As used herein, the term "hydrocarbon product" refers to the product obtained by contacting the feed with the catalyst in the presence of hydrogen and under the reaction conditions discussed below. The hydrocarbon product has at least a 5:1 ratio of even-numbered alkanes to odd-numbered alkanes and comprises at least one linear alkane of $C_n$ chain length, wherein n=10, 12, 14, 16 or 18.

As used herein, the term "residual hydrocarbon product" refers to the collective portions of the hydrocarbon product which remain after separation of the desired $C_n$ alkane(s) in sufficient purity for fermentation to linear dicarboxylic acids of the same $C_n$ chain length(s). For example, when the desired $C_n$ alkane(s) are separated from the hydrocarbon product by distillation, the distillate fractions and distillation bottoms which do not contain the desired $C_n$ alkane(s) in sufficient purity for fermentation to linear dicarboxylic acids of the same $C_n$ chain length(s) are termed the residual hydrocarbon product.

As used herein, the term "linear dicarboxylic acid" refers to unbranched dicarboxylic acids of the form $HO(O)C(CH_2)_mC(O)OH$, where m specifies the number of methylene units. Such compounds are also referred to as dicarboxylic acids. The term "linear dicarboxylic acid of $C_n$ chain length" refers to an unbranched dicarboxylic acid having n number of total carbons, including the carbons of the terminal carboxyl groups, where n=10, 12, 14, 16 or 18.

The value for n (n=10, 12, 14, 16 or 18) specifies the carbon chain length of the chemical to which it refers, for example a fatty acid, an alkane, or a dicarboxylic acid. The method disclosed herein of making a linear dicarboxylic acid of $C_n$ chain length provides the dicarboxylic acid in high purity, substantially free of dicarboxylic acids having other chain lengths. It is contemplated that the feed and the hydrocarbon product from which the dicarboxylic acid is produced may contain more than one fatty acid or alkane of $C_n$ chain length and that the disclosed method can provide, separately, more than one dicarboxylic acid of $C_n$ chain length. For example, a feed may comprise $C_{12}$ and $C_{14}$ fatty acids and may be hydrotreated to a hydrocarbon product comprising $C_{12}$ and $C_{14}$ alkanes, which can be separated and independently fermented to $C_{12}$ and $C_{14}$ dicarboxylic acids.

As used herein, the term "linear dicarboxylic acid of $C_n$ chain length where n=10", also referred to as $C_{10}$ dicarboxylic acid, refers to sebacic acid, which is also known as decanedioic acid or 1,8-octanedicarboxylic acid.

As used herein, the term "linear dicarboxylic acid of $C_n$ chain length where n=12", also referred to as $C_{12}$ dicarboxylic acid, refers to 1,12-dodecanedioic acid, which is also known as 1,10-decanedicarboxylic acid.

As used herein, the term "linear dicarboxylic acid of $C_n$ chain length where n=14", also referred to as $C_{14}$ dicarboxylic acid, refers to tetradecanedioic acid, which is also known as 1,12-dodecanedicarboxylic acid.

As used herein, the term "linear dicarboxylic acid of $C_n$ chain length where n=16", also referred to as $C_{16}$ dicarboxylic acid, refers to hexadecane-1,16-dioic acid, which is also known as 1,14-tetradecanedicarboxylic acid or thapsic acid.

As used herein, the term "linear dicarboxylic acid of $C_n$ chain length where n=18", also referred to as $C_{18}$ dicarboxylic acid, refers to octadecane-1,18-dioic acid, which is also known as 1,16-hexadecanedicarboxylic acid.

As used herein, the term "fatty acid" refers to a monocarboxylic acid with an unbranched aliphatic tail, or chain. The term "linear carboxylic acid of $C_n$ chain length" refers to an unbranched carboxylic acid having n number of total carbons, including the carbon of the terminal carboxyl group. Fatty acids are derived from or contained in esterified form in an animal or vegetable fat, oil, or wax. Natural fatty acids commonly have a chain length of 4 to 28 carbon atoms. Fatty acids can be bound to other molecules, such as in triglycerides.

As used herein, the term "free fatty acid" refers to fatty acids which are not bound to other molecules. A free fatty acid is obtained, for example, when a triglyceride is broken down into its components (fatty acids and glycerol).

As used herein, the term "linear fatty acid of $C_n$ chain length where n=10", also referred to as $C_{10}$ fatty acid, refers to decanoic acid, also known as capric acid.

As used herein, the term "linear fatty acid of $C_n$ chain length where n=12", also referred to as $C_{12}$ fatty acid, refers to dodecanoic acid, also known as lauric acid.

As used herein, the term "linear fatty acid of $C_n$ chain length where n=14", also referred to as $C_{14}$ fatty acid, refers to tetradecanoic acid, also known as myristic acid.

As used herein, the term the "linear fatty acid of $C_n$ chain length where n=16", also referred to as $C_{16}$ fatty acid, refers to hexadecanoic acid, also known as palmitic acid.

As used herein, the term "linear fatty acid of $C_n$ chain length where n=18", also referred to as $C_{18}$ fatty acid, refers to octadecanoic acid, also known as stearic acid.

As used herein, the term "triglyceride" refers to a glyceride formed by esterification of a glycerol molecule with three fatty acids. The three fatty acids can be all different, all the same, or only two the same. Triglycerides are the main constituent of vegetable oil and animal fats.

As used herein, the term "tallow" refers to animal fats and includes mutton fat, beef fat, and pig fat (lard).

As used herein, the term "poultry fat" refers to animal fat obtained from poultry.

As used herein, the term "yellow grease" refers to waste vegetable oil, which can be obtained from industrial deep fryers in potato processing plants, snack food factories, and fast food restaurants, for example.

As used herein, the term "green diesel" refers to diesel from renewable resources. Obtaining green diesel involves converting the fatty acids in triglycerides into linear alkanes via hydrodeoxygenation (HDO). The triglyceride backbone is converted to propane and separated. Green diesel can be used as a fuel by itself or as a mixture with diesel from petroleum feedstocks (petro diesel) with little to no engine modification and can be processed in refineries currently refining crude oils. Current processes involve multiple steps, including hydrodeoxygenation, hydroisomerization, and/or hydrocracking, to obtain green diesel fuel having properties comparable to those of petro diesel.

As used herein, "ATCC" refers to the American Type Culture Collection International Depository located at 10801 University Boulevard, Manassas, Va. 20110-2209 U.S.A. The "ATCC No." is the accession number to cultures on deposit with the ATCC.

*Pichia pastoris* SW64/65, identified as ATCC No. 74409, is characterized as a *Pichia pastoris* strain that has the ability, when induced by the presence of methanol, to produce active alkane cytochrome P450s that will convert $C_6$ to $C_{22}$ alkanes to the corresponding mono and diacids.

*Candida maltosa* SW81/82, identified as ATCC No. 74431, is characterized as a *Candida maltosa* that does not grow on $C_6$ to $C_{22}$ alkanes or monofatty acids, but does have the ability to produce diacids from $C_6$ to $C_{22}$ monoacids or alkanes in the presence of suitable carbon and energy sources such as glycerol. This strain contains disrupted POX4 genes and has other auxotrophic markers removed. This strain is β-oxidation blocked.

*Candida maltosa* SW 84/87.2, identified as ATCC No. 74430, is characterized as a *Candida maltosa* that does not grow on $C_6$ to $C_{22}$ alkanes or monofatty acids, but does have the ability to produce diacids from $C_6$ to $C_{22}$ monoacids or alkanes in the presence of suitable carbon and energy sources such as glycerol. In addition, SW84/87.2 does have the ability to oxidize $C_6$ to $C_{22}$ alkanes or monoacids to diacids in the presence of glucose at greater than 5 g/L concentration. This strain expresses enhanced alkane hydroxylating activity and contains disrupted POX4 genes.

As used herein, "reduced nicotinamide-adenine dinucleotide" is abbreviated as NADH.

As used herein, "reduced nicotinamide-adenine dinucleotide phosphate" is abbreviated as NADPH.

As used herein, "*Candida maltosa* IAM12247 cytochrome P450Alk1-A gene" is abbreviated as Alk1-A.

As used herein, "*Candida maltosa* IAM12247 cytochrome P450Alk3-A gene" is abbreviated as Alk3-A.

As used herein, "*Candida maltosa* cytochrome P450-NADPH reductase gene" is abbreviated as P450 reductase or CPR.

As used herein, "*Candida maltosa* acyl CoA gene" is abbreviated as POX4.

As used herein, "*Candida maltosa* IAM12247 URA3 gene codes for the enzyme orotidine-5'-monophosphate decarboxylase" is abbreviated as URA3.

As used herein, "phosphoglycerol kinase" is abbreviated PGK.

As used herein, "alcohol oxidase I" is abbreviated as AOX1.

As used herein, "gas chromatography" is abbreviated as GC.

As used herein, "polymerase chain reaction" is abbreviated as PCR.

As used herein, "autonomously replicating sequences" is abbreviated as ARS.

The term "genetically-engineered" refers to the formation of new combinations of heritable material by the insertion of nucleic acid molecules, produced or derived by whatever means outside the cell, into any virus, bacterial plasmid or other vector system so as to allow their incorporation into a host organism in which they are propagated and expressed to alter the phenotype of the host organism.

The term "transformation" refers to genetic engineering in which a nucleic acid fragment is transferred into the genome of a host organism, resulting in genetically stable inheritance. Host organisms containing the transferred nucleic acid fragments are referred to as "transgenic" or "transformed" organisms or transformants.

The term "nucleic acid" refers to complex compounds of high molecular weight occurring in living cells, the fundamental units of which are nucleotides linked together with phosphate bridges. Nucleic acids are subdivided into two types: ribonucleic acid (RNA) and deoxyribonucleic acid (DNA).

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "cytochrome P450" refers to a widely distributed monooxygenase, active in many different biological hydroxylation reactions and one component of the cytochrome P450 hydroxylating system.

The term "cytochrome P450 reductase" refers to a widely distributed reductase, active in many different biological hydroxylation reactions and one component of the cytochrome P450 hydroxylating system.

The terms "blocked β-oxidation pathway" and "β-blocked" refer to gene disruptions that effectively eliminate acyl-CoA oxidase, the first enzyme in the β-oxidation pathway of a wild-type.

"Altered levels" refers to the production of gene product(s) in organisms in amounts or proportions that differ from that of normal, wild-type, or non-transformed organisms. Production may be more specifically described as "enhanced" or "decreased" relative to that of normal, wild-type, non-transformed organisms.

The term "enhanced" refers to an improvement or increase over an original observation or function. Enhanced alkane hydroxylating activity is associated with at least one additional copy of genes (relative to the wildtype) encoding cytochromes P450 monooxygenase and/or cytochrome P450-NADPH reductase.

The terms "cassette" and "gene cassette" refer to a number of nucleotide sequences which have been deliberately joined or combined in-vitro into a unique construction. An "expression cassette" specifically includes a promoter fragment, a DNA sequence for a selected gene product and a transcription terminator.

The terms "plasmid" and "cloning vector" refer to an extra chromosomal element usually in the form of circular double-stranded DNA molecules and often carrying genes which are not part of the central metabolism of the cell. Such elements may be autonomously replicating sequences, genome integrating sequences, phage sequences, linear or circular, of a single- or double-stranded DNA or RNA, derived from any source. The term "autonomously replicating sequence" refers to chromosomal sequences with the ability to allow autonomous replication of plasmids in yeasts.

The term "expression" refers to the transcription and stable accumulation of sense (mRNA) or antisense RNA derived from the nucleic acid fragment of the invention. Expression may also refer to translation of mRNA into a polypeptide. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

The term "mutation" refers to a chemical change in the DNA of an organism leading to a change in the genetic character of the organism. A strain exhibiting such a changed characteristic is termed a "mutant".

The term "oligonucleotide primer" refers to a short oligonucleotide that base-pairs to a region of single-stranded template oligonucleotide. Primers are necessary to form the starting point for DNA polymerase to produce complementary-stranded synthesis with single-stranded DNA.

The terms "restriction enzyme" and "restriction endonuclease" refer to an enzyme which catalyzes hydrolytic cleavage within a specific nucleotide sequence in double-stranded DNA.

The term "straight chain hydrocarbon" refers to aliphatic hydrocarbons, fatty acids, and esters of fatty acids of carbon number $C_6$ to $C_{22}$ containing 0, 1 or 2 double bonds in the carbon backbone. In addition, the term includes any of the straight chain compounds described above where one of the terminal carbons has been replaced by a phenyl group. Specific preferred hydrocarbons are nonane, decane, undecane, dodecane, tridecane, tetradecane, pentadecane, hexadecane, heptadecane, octadecane or any of the respective mono-carboxylic acids. Preferred are $C_{12}$-$C_{14}$ alkanes. Dodecane is especially preferred.

The term "alkane hydroxylating activity" refers to the ability of an organism, such as a yeast, to enzymatically hydroxylate the terminal methyl group of a straight-chain hydrocarbon using a cytochrome P450 hydroxylating system. The term "cytochrome P450 hydroxylating system" refers to a hydroxylating system composed of at least the following three biological components: 1) cytochrome P450 monooxygenase, 2) cytochrome P450-NADPH reductase and 3) reduced nicotinamide-adenine dinucleotide (NADH) or reduced nicotinamide-adenine dinucleotide phosphate (NADPH).

"Gene" refers to a nucleic acid fragment that encodes a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. An "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. Different promoters may direct the expression of a gene in different tissues or cell types, or at different stages of development, or in response to different environmental conditions. Promoters which cause a gene to be expressed under most growth conditions at most times are commonly referred to as "constitutive promoters". New promoters of various types useful in plant cells are constantly being discovered; numerous examples may be found in the compilation by Okamuro and Goldberg, (*Biochemistry of Plants* 15:1-82 (1989)). However, since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

"Mature" protein refers to a post-translationally processed polypeptide; i.e. one from which any pre- or propeptides present in the primary translation product have been removed. "Precursor" protein refers to the primary product of translation of mRNA; i.e. with pre- and propeptides still present. Pre- and propeptides may be but are not limited to intracellular localization signals.

Feed

The feed is a renewable resource and may be any plant or animal derived oils, fats, free fatty acids, alkyl esters, or a combination of these.

The renewable resource may be an oil derived from plants and/or animals and comprising one or more free fatty acids, the oil comprising at least about 5 mole %, for example at least about 10 mole %, or at least about 15 mole %, or at least about 20 mole %, or at least about 25 mole %, or at least about 30 mole %, or at least about 35 mole %, or at least about 40% of a linear fatty acid of $C_n$ chain length, where n=10, 12, 14, 16, or 18. The feed may comprise a mixture of free fatty acids. For example, the feed may comprise lauric acid, myristic acid, palmitic acid, or a combination of these.

The renewable resource may be an oil derived from plants and/or animals and comprising one or more triglycerides, where the oil comprises at least about 5 mole %, for example at least about 10 mole %, or at least about 15 mole %, or at least about 20 mole %, or at least about 25 mole %, or at least about 30 mole %, or at least about 35 mole %, or at least about 40 mole % of a triglyceride derived from a linear fatty acid of $C_n$ chain length, where n=10, 12, 14, 16, or 18. The feed may comprise a mixture of triglycerides. These triglycerides may be derived from a plant selected from the group consisting of pine, rape seed, canola, sunflower, jathropa, seashore mallow and combinations of two or more thereof. Oil from genetically modified plant varieties may also be used, for example genetically modified high stearic acid or high lauric acid canola varieties.

The feed may be a vegetable oil selected from the group consisting of coconut oil, palm kernel oil, palm oil, soybean oil, cottonseed oil, and combinations of two or more of these. The feed may comprise poultry fat, yellow grease, tallow, or a combination of these. The feed may also comprise used vegetable oils or oils from pyrolysis of biomass. The feed may also comprise oils derived from marine life, such as algae.

The renewable resource may also be an alkyl ester of a fatty acid derived from triglycerides, the ester comprising at least about 5 mole %, for example at least about 10 mole %, or at least about 15 mole %, or at least about 20 mole %, or at least about 25 mole %, or at least about 30 mole %, or at least about 35 mole %, or at least about 40% of an ester of a linear fatty acid of $C_n$ chain length, where n=10, 12, 14, 16, or 18. The alkyl group may be a $C_1$-$C_{10}$ alkyl group, for example methyl. The feed may comprise a mixture of esters.

Transesterification of fatty acids in triglycerides into methyl esters using methanol and a catalyst such as sodium methylate, produces FAME (Fatty Acid Methyl Ester), which is commonly referred to as bio-diesel. These methyl esters, mainly linear $C_{14}$ to $C_{22}$ carboxylic acids, can be used as fuel or can be blended into diesel refined from crude oil sources.

The feed may also be a renewable resource obtained from a bio-diesel or green diesel process, for example a product or process stream comprising a linear alkane of $C_n$ chain length, where the chain length of the alkane corresponds to the chain length of the desired linear dicarboxylic acid. Diesel from renewable resources, commonly referred to as green diesel, involves converting the fatty acids in triglycerides into linear alkanes via hydrodeoxygenation (HDO). The triglyceride backbone is converted to propane and separated.

The hydrotreating process by which the feed is converted to a hydrocarbon product is flexible and selection of the feed may be based on its content of $C_n$ fatty acid, where the chain length of the fatty acid corresponds to the chain length of the desired linear dicarboxylic acid, as well as its availability and cost. The selection of the feed may also be based on the value or usefulness of the other hydrocarbons obtained from the hydrodeoxygenation process, the alkanes which are not fermented to the desired linear dicarboxylic acids and which are referred to collectively as "residual hydrocarbon product".

The residual hydrocarbon product may be used as green diesel, for example, or as a feed in a process to produce green diesel. The residual hydrocarbon product may also be used as blending stock for (petro) diesel fuel. Thus, feed selection may also be based on the overall economics of production of the desired linear dicarboxylic acid(s) in combination with the energy value of the residual hydrocarbon product. As a result, in some cases, an oil comprising less than about 5 mole % of the desired linear fatty acid, or less than about 5 mole % of a triglyceride derived from a linear fatty acid, may be used as a feed. Likewise, in some cases, an oil comprising greater than about 40 mole % of the linear fatty acid, or greater than about 40 mole % of a triglyceride derived from a linear fatty acid, may also be used. Depending on the feed, the hydrocarbon product obtained in the hydrotreating process may comprise a linear alkane of other chain lengths, for example a $C_8$ or $C_{20}$ alkane. For ease of handling, the feed may be used as a liquid feed.

Catalyst

Delmon, B. "Catalysts in Petroleum Refining 1989" in: Studies in Surface Science and Catalysis, Eds. Trimm, D. L., Akashah, S., Absi-Halabi, M., and Bishara, A. (Elsevier, Amsterdam, 1990), pp 1-38, discloses the transformation of a very large portion of crude oil to usable products, which depends on cracking and hydrotreating processes. Over the last several decades, hydrotreating processes have become more complex and diversified and include such processes as hydropurification (e.g., removal of sulfur, nitrogen, oxygen, metals, etc.), hydroconversion (e.g., production of jet fuels or lubricants), and hydrocracking (mild or heavy hydrocracking) Specifically, the removal of sulfur, nitrogen, oxygen, and metals are called hydrodesulfurization, hydrodenitrogenation, hydrodeoxygenation, and hydrodemetallization, respectively.

Certain hydrotreating catalysts for use with petroleum feedstocks typically comprise one or more non-precious metals such as nickel, cobalt, molybdenum and tungsten supported on mono- or mixed-metal oxides such as alumina, silica or silica-alumina. The catalysts can be promoted by Group I metals (e.g., lithium, sodium and potassium) and/or fluorine, boron, and phosphorus. The catalyst is activated by simultaneous reduction and sulfidation in place before subjecting it to hydrotreating reactions. Catalysts consisting of molybdenum supported on alpha-alumina with promoters such as cobalt (Co—Mo/$Al_2O_3$) or nickel (Ni—Mo/$Al_2O_3$) are extensively used in the hydrotreating of petroleum fractions and resids.

The catalyst most commonly used for the production of diesel from renewable resources comprises a precious metal such as platinum and/or palladium. Murzin et al. in Industrial Engineering Chemical Research, Vol. 45 (2006) pp. 5708-5715, disclose numerous metals used for such catalysis. Platinum and palladium gave the best conversion of desired products. Nickel catalysts produced unwanted heavier products such as dimers due to the recombination of moieties resulting from extensive cracking of the feed material.

In the methods hereof, the catalyst comprises an active metal and an oxide. The active metal may be one or more non-precious metals. The oxide comprises a mono- or mixed metal oxide and is used as a support. The active metals may be nickel (Ni), cobalt (Co), molybdenum (Mo), tungsten (W), or mixtures thereof, e.g., nickel-molybdenum (NiMo), cobalt-molybdenum (CoMo). Preferably, the active metal is Ni. The metal(s) may be either in the reduced or sulfided (e.g., $Ni_9S_8$, $Co_9S_8$, $MoS_2$) form. When the active metal is nickel, higher amounts, such as at least 40 wt %, may be needed to reduce in the presence of alumina as the support.

In a reducing step, the catalyst is treated with hydrogen, preferably at elevated temperatures, such as from 100° C. to 400° C. Typically the catalyst temperature is increased during hydrogen flow, such as starting at a temperature of about 130° C. and increasing to a temperature of 250° C. or 350° C. Such methods are known to those skilled in the art. A particular procedure for reducing catalyst is provided below in the Examples.

The catalyst may be sulfided by contacting the prepared catalyst with a sulfur-containing compound such as thiols, sulfides, disulfides, $H_2S$, or combinations thereof at elevated temperatures. The catalyst may be sulfided before it is used or during the hydrotreating process by introducing a small amount of sulfur-containing compounds, such as thiols, sulfides, disulfides, $H_2S$, poultry fat, or combinations of two or more thereof, in the feed. Sulfiding may contribute to the long term activity of the catalyst, depending on reaction conditions and feed compositions. A detailed sulfiding procedure is described below in the examples.

Optionally, a metal promoter may be used with the active metal in the processes provided by this invention. Suitable metal promoters include: 1) those elements from Groups 1 and 2 of the periodic table; 2) tin, copper, gold, silver, and combinations thereof; and 3) combinations of group 8 metals of the periodic table in lesser amounts. The active metal, including whether reduced or sulfided, will be selected based on the desired product.

The oxide may include a mono- or mixed-metal oxide used as a support for the active metal. Materials frequently used as the oxide are porous solids with high total surface areas (external and internal) which can provide high concentrations of active sites per unit weight of catalyst. The oxide has the ability to enhance the function of the active metal; and supported catalysts are generally preferred because the metal is used more efficiently.

The oxide may include a porous solid oxide with high total surface areas (external and internal) which can provide high concentrations of active sites per unit weight of catalyst. Preferably the oxide has pores of a relatively small diameter that is preferably 50 nm or less. Preferred oxides have a surface area greater than 20 $m^2$/g, more preferably, the oxide has a surface area greater than 75 $m^2$/g, still more preferably the oxide has a surface area of at least 100 $m^2$/g. Generally surface area is less than 300 $m^2$/g.

The oxide may be a porous solid oxide with high surface area including, but not limited to, oxides such as silica, alumina, titania, titania-alumina, titania-silica, calcium oxide, barium oxide, zirconia, lanthanum oxide, magnesium oxide, kieselguhr, silica-alumina, zinc oxide, and combinations thereof. The oxide is preferably selected from the group consisting of alumina, silica, titania, zirconia, kieselguhr, silica-alumina, and combinations thereof. More preferably the oxide is alumina, silica, kieselguhr, or a combination thereof.

The catalyst may further comprise other materials including carbon, such as activated charcoal, graphite, and fibril nanotube carbon, as well as calcium carbonate, calcium silicate and barium sulfate.

The catalyst may be prepared using any of a variety of ways known in the art. Preferably, a preformed (e.g., already calcined) metal oxide is used. For example, the metal oxide is preferably calcined before application of the active metal. The method of placing the active metal on the metal oxide is not critical. Several methods are known in the art. Many suitable catalysts are available commercially.

Relative proportions of active metal and oxide, while not critical, are important in that if too little active metal is present, initial activity will be lower than desired and a long activation period may be required for the catalyst to reach maximum activity. It will be appreciated that the higher the weight percent of active metal, the faster the reaction. A preferred content range of the active metal in the catalyst is from about 0.1 wt % to about 90 percent by weight of the total supported catalyst. A more preferred active metal content range is from about 0.2 wt % to about 75 wt %. A further preferred active metal content range is from about 0.5 wt % to about 60 wt %.

In the hydrotreating process of the method of the invention, a hydrocarbon is produced having a higher ratio of even-numbered to odd-numbered hydrocarbons. In this process, the active metal preferably comprises nickel, cobalt and molybdenum. The nickel content of the catalyst for this process is generally between 0.2 wt % and 20 wt %, more preferably, between 0.5 wt % and 15 wt %.

Hydrotreating Process

The hydrotreating process may comprise, but is not limited to, three major reactions: hydrodeoxygenation (HDO), hydroisomerization (HI) and/or hydrocracking (HC). Minor reactions can occur during these steps without significantly altering the desired product.

The HDO process is the removal of oxygen from the fatty acids in triglycerides and other free fatty acids to produce a paraffin (hydrocarbon) product. The HDO can occur either as a decarbonylation, decarboxylation or hydrodeoxygenation or a combination thereof. Decarboxylation refers to the process of removal of oxygen as carbon dioxide producing a paraffinic hydrocarbon. Decarbonylation refers to the process of removal of the oxygen as carbon monoxide and water directly creating an unsaturated hydrocarbon or indirectly by adding hydrogen to produce a saturated hydrocarbon. Hydrodeoxygenation refers to the process of removal of oxygen as water by adding hydrogen. In decarboxylation and decarbonylation, the resulting paraffinic hydrocarbon is one carbon unit shorter than the corresponding carboxylic acid. In hydrodeoxygenation, the resulting hydrocarbon has the same number of carbons as the corresponding carboxylic acid.

Advantageously, the hydrotreating process may be tailored to control the route of oxygen removal. For processes that make minimal use of hydrogen, the decarboxylation and direct decarbonylation routes can be used. For a process that makes minimal evolution of carbon monoxide and carbon dioxide, the indirect decarbonylation or hydrodeoxygenation are the preferred routes. Hydrodeoxygenation is also the preferred route when it is desired to avoid carbon-carbon bond scission and to maintain the same number of carbon atoms in the linear backbone of the alkane (and ultimately the dicarboxylic acid) as in a fatty acid contained in the feed.

The chain length may play an important role in determining which particular deoxygenation process to use. For example, producing $C_{11}$ removes oxygen from the fatty acid primarily as CO and/or $CO_2$ (reduced hydrogen consumption) whereas making $C_{12}$ removes oxygen primarily in the form of $H_2O$ (reduced greenhouse gas emissions). Depending on a particular application, one may prefer $C_{11}$ or $C_{12}$ linear hydrocarbon. These routes can be selectively controlled by varying the type and/or composition of the catalyst as described herein. Reduced supported metal oxide catalysts can be used when lower ratio of even to odd linear hydrocarbon is desired; whereas, sulfided supported mixed metal oxide catalysts can be used when higher ratio of even to odd linear hydrocarbon is desired.

Hydrotreatment, as described in the methods hereof, includes contacting the feed with hydrogen at elevated temperatures and pressures in the presence of the disclosed catalyst compositions, to hydrodeoxygenate, hydroisomerize and/or hydrocrack the feed into the desired fuel. Temperatures range from 250 to 425° C., preferably at 275 to 400° C., most preferably from 300 to 375° C. Pressures range from 500 to 2500 psig (3,450 to 17,250 kPa), preferably 1000 to 2000 psig (6,900 to 13,900 kPa).

In an another embodiment of the hydrotreating process, a process for hydrodeoxygenation of a renewable resource is provided, which comprises (a) providing a feed which is a renewable resource; (b) contacting the feed with a catalyst in the presence of hydrogen at a temperature of 250 to 425° C. and a pressure of 500 to 2500 psig (3,450 to 17,250 kPa), wherein the catalyst comprises molybdenum and one or more active metals selected from the group consisting of nickel, cobalt, or mixtures thereof and the catalyst is sulfided prior to use, to produce a hydrocarbon product having a ratio of even-numbered hydrocarbons to odd-numbered hydrocarbons of at least 1:1, preferably at least 3:1, more preferably at least 5:1 and most preferably at least 10:1. Preferably, the catalyst comprises nickel, cobalt and molybdenum.

Surprisingly, use of non-precious metals such as nickel, cobalt, molybdenum, or combinations thereof in the hydrotreating process of this method produces yields of hydrotreated product equivalent to or better than yields produced using the more expensive, precious metal catalysts such as disclosed in U.S. Patent Publication 2006/0207166.

The methods hereof may be performed in any suitable type of reactor, which include a fixed bed reactor and a slurry reactor. A fixed bed reactor has an advantage of easy separation of the reactants and products from the catalyst. Fixed bed reactors include plug flow and trickle bed reactors. Fixed bed reactors can be of the type adiabatic, multi-tubular, continuous recirculating packed bed reactor. Slurry reactors include batch, a continuously stirred tank reactor, and a bubble column reactor. In the slurry reactors, the catalyst may be removed from the reaction mixture by filtration or centrifugal action. Preferably, the process of this invention is a continuous process and the reactor is a fixed bed or continuously stirred tank reactor. More preferably, the process is a continuous process and the reactor is a fixed bed reactor.

Preferably, the process is a continuous process in a fixed bed or slurry reactor and the catalyst is in the form of particles, preferably shaped particles. By "shaped particle" it is meant the catalyst is in the form of an extrudate. Extrudates include cylinders, pellets, or spheres. Cylinder shapes may have hollow interiors with one or more reinforcing ribs. Trilobe, cloverleaf, rectangular- and triangular-shaped tubes, cross, and "C"-shaped catalysts can be used.

Preferably the shaped catalyst particle is about 0.01 to about 0.5 inch (about 0.25 to about 13 mm) in diameter when a packed bed reactor is used. More preferably, the catalyst particle is about 1/32 to about 1/4 inch (about 0.79 to about 6.4 mm) in diameter.

A wide range of suitable catalyst concentrations may be used. The amount of catalyst per reactor is generally dependent on the reactor type. For a fixed bed reactor, the volume of catalyst per reactor will be high, while in a slurry reactor, the volume will be lower. Typically, in a slurry reactor, the catalyst will make up 0.1 to about 30 wt % of the reactor contents. Preferably, the catalyst is 1 to 15 wt % of the reactor contents.

For a fixed bed reactor, the weight hourly space velocity will typically fall in the range of 0.05 to 100 $hr^{-1}$, preferably, 0.1 to 10 $hr^{-1}$, more preferably 1.0 to 5.0 $hr^{-1}$.

In one embodiment of the hydrotreating process of the methods hereof, the feed is contacted with hydrogen to form a liquid feed/hydrogen mixture in advance of contacting the liquid feed/hydrogen mixture with the catalyst. Optionally, a solvent or diluent, having a relatively high solubility for hydrogen so that substantially all the hydrogen is in solution, can be added to the feed and hydrogen in advance of contacting with the catalyst to form a liquid feed/solvent or liquid feed/diluent mixture. The liquid feed/solvent or liquid feed/diluent mixture is then contacted with hydrogen to form a liquid feed/solvent/hydrogen or liquid feed/diluent/hydrogen mixture. The mixture containing hydrogen is then contacted with the catalyst.

In a preferred process, the liquid feed/solvent/hydrogen or liquid feed/diluent/hydrogen mixture is contacted with catalyst in a packed bed reactor, such as plug flow, tubular or other fixed bed reactor for feed and hydrogen to react. The packed bed reactor may be a single packed bed or multiple beds in series or in parallel or in a combination thereof as discussed hereinabove.

The liquid feed/solvent/hydrogen or liquid feed/diluent/hydrogen mixture can be a substantially hydrogen-gas-free liquid feed stream. The feed stream can be produced by contacting liquid feed with hydrogen and solvent or diluent to produce a hydrogen-saturated liquid feed. Alternatively or in addition, after contacting liquid feed with hydrogen and solvent or diluent, hydrogen gas can be removed from the feed stream, for example, by known gas/liquid separation methods in a disengagement step. Processes for producing hydrogen-gas-free liquid feed streams are known, such as those disclosed in U.S. Pat. Nos. 6,123,835; 6,428,686; 6,881,326 and 7,291,257.

The percentage of hydrogen soluble in the solvent/diluent is greater than the percentage of hydrogen soluble in the liquid feed reactant. In this embodiment, preferably all of the hydrogen required for reaction is made available in solution upstream of the fixed bed reactor, thus eliminating the need to circulate hydrogen gas within the reactor.

The reaction of liquid feed/solvent/hydrogen or liquid feed/diluent/hydrogen mixture with catalyst is highly exothermic and as a result a great deal of heat is generated in the reactor. The temperature of the reactor may be controlled by using a recycle stream. A portion of the paraffin (hydrocarbon) product, (reactor effluent) may be recycled back to the front of the reactor as a recycle stream and blended with fresh feed and hydrogen for use as solvent or diluent.

The process may be a multi-stage process using a series of two or more reactors in series and fresh hydrogen may be added at the inlet of each reactor. The recycle stream absorbs some of the heat and reduces the temperature rise through the reactor. The reactor temperature may be controlled by controlling the fresh feed temperature and the amount of recycle. In addition, because the recycle stream comprises reacted components, the recycle stream also serves as an inert diluent.

The type and amount of diluent added, as well as the reactor conditions can be set so that substantially all of the hydrogen required in the hydrotreating reactions is available in solution. The solvent or diluent is preferably a portion of the reactor effluent used as a recycle stream, but can alternatively be selected from the group consisting of light hydrocarbons, light distillates, naphtha, diesel, or the like. Examples include propane, butanes, and/or pentanes. The percentage of hydrogen in the solvent or diluent is greater than the percentage of hydrogen in the feed, thus, in this embodiment, all of the hydrogen required for reaction is made available in solution upstream of the reactor and eliminating the need to re-circulate hydrogen gas co-eluting with the effluent or product stream.

Separation of the Alkane

The hydrocarbon product obtained by contacting the feed with the catalyst in the presence of hydrogen under the appropriate reaction conditions comprises a linear alkane of $C_n$ chain length, where n=10, 12, 14, 16 or 18. Depending on the feed, the hydrocarbon product may comprise a linear alkane of other carbon chain lengths, for example a $C_8$ or $C_{20}$ alkane.

Normal paraffins in the $C_9$-$C_{17}$ range are generally isolated by close-cut distillation, followed by isolation from branched-chain hydrocarbons and aromatics by selective adsorption with molecular sieves. These molecular sieves are synthetic zeolites that have a series of central cavities interconnected by pores. The pores have uniform diameters that are large enough to permit passage of only the smaller-diameter, unbranched paraffins. The bulkier components, such as isoparaffins, cycloparaffins, and aromatics, are excluded and are not adsorbed internally by the molecular sieves. The normal paraffins are desorbed later to produce a 97-99% assay normal product.

Commercial isolation processes using molecular sieves include IsoSiv® (Dow Chemical Company), Molex® (UOP LLC) and Ensorb® (Exxon Mobil Corporation). The feedstock for an n-paraffin extraction unit is usually desulfurized by conventional technology and fractionated so as to include the range of normal paraffins (carbon numbers) of the desired output. The extraction is accomplished in either the liquid phase (Molex®) or the vapor phase (Ensorb®, IsoSiv®). Desorption of the n-paraffins may be accomplished by displacement with a lower-molecular-weight n-paraffin such as heptane, octane or isooctane (Molex®) or with a polar desorbent such as ammonia (Ensorb®, IsoSiv®).

The various extraction processes may differ in their sensitivity to feed impurities such as aromatics and sulfur or in the rate of coking on the molecular sieves, but are believed to be capable of producing comparable products. A product containing 98% n-paraffins may be made from a kerosene/gas oil fraction containing a wide range (15-25%) of normal $C_9$-$C_{17}$ paraffins by volume. The yield represents approximately 98% recovery of the n-paraffins in the feed. The isolated normal paraffins are generally fractionally distilled to produce a close cut of the particular mixture of n-paraffins required for a specific end use and consumer specifications. However, the above commercial processes require expensive and extensive purification and separation steps, large quantities of molecular sieves or other separation media, and extremely inefficacious for products containing high ratios of linear to branched alkanes.

Surprisingly, it was observed that in the processes hereof the desired linear alkane(s) of $C_n$ chain length can be isolated efficaciously from alkane mixtures of linear and branched isomers as one or more distillate fractions via one or more distillations as opposed to current commercial processes which use an expensive selective adsorption technique. Optionally, further distillation may be performed to obtain the desired linear alkane(s) in the desired purity.

The distillation may be performed in a continuous manner using one or more distillation columns, or in a batch manner using a single column. Although many continuous distillation configurations may be used, a desirable configuration is to remove low boiling impurities overhead in a first distillation column with collection of the product and high boilers from the re-boiler. The product cut may then be collected overhead in a second distillation column with a high boiling impurity purge from the re-boiler.

Distillation columns using random packing, structured packing, or trays, for example, may be used for the separation. For continuous distillation, columns containing 1 to 100 equilibrium stages, or for example 5 to 50 equilibrium stages, or for example 20 to 30 equilibrium stages, are desirable to maximize product yield without excessive column height. Continuous distillation columns may be fed at any position along the column length, but feed near the center of each column is preferred. Vapor or liquid feeds to the column and vapor or liquid removal from the column as distillate or heels maybe used. Desired reflux ratios for continuous distillation are in the range of 1-50, or for example 5-30, or for example 10-20, to maximize purity and capacity with minimal column diameter. The distillation may be performed under positive pressure, at atmospheric pressure, or under reduced pressure. Operating pressure of 10-250 mm Hg (absolute) is preferred with 20-100 mm Hg (absolute) most preferred to prevent excessive pot temperatures. The re-boiler may be heated with steam, electricity, or other suitable heat transfer media. The condenser may be cooled with water, air, or a suitable heat transfer media.

Batch distillation may also be used for product purification through collection of a foreshot cut overhead to remove low boiling impurities, followed by collection of the pot liquid as the product. Optionally, a product cut may be taken overhead to separate the product from high boiling impurities. For batch distillation, columns containing 1-50 equilibrium stages, or for example 5-30 equilibrium stages, or for example 10-25 equilibrium stages, are desirable. Reflux ratios of 0.2 to 50, for example 2 to 30, or for example 10 to 25 are desirable to maximize purity and minimize yield loss with minimal equipment size and batch cycle time. During the main product cut, lower reflux ratios may be used to minimize cycle time followed by an increase in the reflux ratio near the end of the product cut to separate high boiling impurities. Operating pressures used for batch distillation are the same as for continuous distillation.

The distillate fractions and distillation bottoms, which do not contain the desired alkane(s) in sufficient purity for fermentation to linear dicarboxylic acids of the same $C_n$ chain length(s), are referred to herein as the "residual hydrocarbon product". At least a portion of the residual hydrocarbon product may be used as fuel for its energy value, for example in a process to produce green diesel or as green diesel. Use of the residual hydrocarbon product in this way minimizes waste of renewable resources and improves the economics of the process for making linear dicarboxylic acids. The residual hydrocarbon product may also be blended with petroleum-based diesel.

The green diesel that can be produced from the residual hydrocarbon product has the desired properties for use as diesel or for blending with petro diesel. The green diesel may be used as fuel alone, or blended in lower cetane products, such as light cycle oil, oil sands or kerosene. (Light cycle oils can not be used as a diesel fuel without the use of cetane enhancing additives.) Hydroisomerization (HI) and hydrocracking (HC) of the residual hydrocarbon product can improve the cold weather properties of the hydrotreated product. In hydroisomerization, a straight chain hydrocarbon is converted into a branched hydrocarbon. Preferably, isomerization is controlled so that the branched hydrocarbon or the mixture of linear and branched hydrocarbons boils in the range of petro diesel. Hydrocracking reduces the chain length. Shorter hydrocarbons provide a lower melting component in green diesel or as an additive to petro diesel. HI and HC both substantially improve the cold weather properties of green diesel by lowering the cloud and pour points.

The green diesel that can be produced from the residual hydrocarbon product raises the cetane number without negatively impacting the density. The substantially linear product has a high cetane number, which is needed to maintain power for diesel engines to run efficiently. Cetane numbers may be controlled by the selection of the specific hydrotreating catalyst and the process conditions. Cetane numbers are desired to be in the range of 50 to 100, more preferably 70 to 100. The branching of some of the chains and the cracking into smaller chains lowers the cloud point temperatures that would allow its usage in cold weather applications down to −40° C., when blended in cold climate petro diesel. The degree of branching is dependent on the temperature of the application and may be controlled by the selection of the hydrotreating catalyst. Green diesel produced by this process also exhibits the desired lubricity (400 to 650 microns), viscosity (3 to 5 cSt at 40° C.), and density (750 to 800 kg/m$^3$ at 25° C.) suitable for today's diesel engines.

One paradigm for a "biomass economy" is the creation of novel successful biorefineries which take advantage of the production of chemical intermediates or building blocks and balance high-value/low-volume products with high-volume/low-value fuels. Biorefineries will not eliminate the need for petrochemicals, but they will play a key role in making the 21st century one of an increasingly sustainable, domestic, and environmentally responsible biomass economy. The linear alkane $C_n$ (where n=10, 12, 14, 16 or 18) of the desired chain length can be coproduced in a green diesel plant. It can be advantageously produced, on-purpose, in a campaign mode by properly selecting the renewable resource for the feed. The desired alkane can be separated from the hydrocarbon product obtained by the hydrotreating process and the residual hydrocarbon product can be blended back with green diesel or petrodiesel fuel. If relatively smaller volumes of linear alkane were required, the desired linear alkane can also be advantageously separated directly from green diesel by fractionation or by batch distillation.

Fermentation

The linear alkane(s) of $C_n$ chain length may be fermented separately to the desired linear dicarboxylic acid(s) of $C_n$ chain length, where n=10, 12, 14, 16 or 18. Methods and microorganisms for fermenting linear alkanes to linear dicarboxylic acids are known, such as those described, for example, in U.S. Pat. Nos. 5,254,466; 5,620,878; 5,648,247, and Published Applications US 2005/0181491 and US 2004/0146999 (each of which is by this reference incorporated in its entirety as a part hereof for all purpose); and in EP 1 273 663. Methods for recovering linear dicarboxylic acids from fermentation broth are also known, as disclosed in at least some of the references cited above and also, for example, in published patent application WO 2000/20620 and U.S. Pat. No. 6,288,275.

US Published Application 2004/0146999 discloses a process for the bioproduction of $C_6$ to $C_{22}$ mono- and di-carboxylic acids by contacting, under aerobic conditions, transformed *Pichia pastoris* characterized by a genetically engineered enhanced alkane hydroxylating activity or transformed *Candida maltosa* characterized by a genetically engineered enhanced alkane hydroxylating activity with at least one $C_6$ to $C_{22}$ straight chain hydrocarbon in the form $CH_3(CH_2)_xCH_3$ wherein x=4 to 20. The reference also discloses a transformed *Pichia pastoris* comprising at least one foreign gene encoding a cytochrome P450 monooxygenase and at least one foreign gene encoding a cytochrome P450 reductase, each gene operably linked to suitable regulatory elements such that alkane hydroxylating activity is enhanced. The genes encoding cytochrome P450s are selected from the group consisting of P450 Alk1-A (D12475(SEQ ID NO:1)), Alk2-A (X55881(SEQ ID NO:2)), Alk3-A (X55881(SEQ ID NO:3)), Alk4-A (D12716 (SEQ ID NO:4)), Alk5-A (D12717(SEQ ID NO:5)), Alk6-A (D12718(SEQ ID NO:6)), Alk7 (D12719(SEQ ID NO:7)) and Alk8 (D12719 (SEQ ID NO:8)) or genes substantially similar thereto.

Also disclosed is a transformed *Candida maltosa* comprising at least one additional copy of genes encoding cytochrome P450 monooxygenases and/or at least one additional copy of genes encoding cytochrome P450 reductase, wherein the genes are operably linked to suitable regulatory elements. Additionally, the reference describes the construction of expression cassettes designed to deregulate expression of the major alkane monooxygenase (P450Alk1-A), fatty acid monooxygenase (P450Alk3-A) and cytochrome P450-NADPH reductase by precise fusion to the *Candida maltosa* phosphoglycerol kinase (PGK) promoter and terminator.

U.S. Ser. No. 04/146,999 also discloses a process for bioproduction of $C_6$ to $C_{22}$ mono- and diterminal carboxylates by contacting, under aerobic conditions, transformed *Candida maltosa* characterized by a genetically-engineered, blocked β-oxidation pathway with at least one $C_6$ to $C_{22}$ straight chain hydrocarbon in the form $CH_3(CH_2)_nCH_3$ where n=4 to 20, as well as a process for bioproduction of $C_6$ to $C_{22}$ mono- and diterminal carboxylates by contacting, under aerobic conditions, transformed *Candida maltosa* characterized by a genetically-engineered, blocked β-oxidation pathway and enhanced alkane hydroxylating activity with at least one $C_6$ to $C_{22}$ straight chain hydrocarbon in the form $CH_3(CH_2)_nCH_3$ where n=4 to 20. Also disclosed are genetically-engineered *Candida maltosa* strains that have enhanced cytochrome P450 activity and/or gene disruptions in the β-oxidation pathway.

U.S. Ser. No. 04/146,999 further discloses novel DNA fragments. These fragments comprise (a) a first *Candida maltosa* promoter operably linked to a DNA encoding at least one polypeptide from *Candida maltosa*, and (b) a second *Candida maltosa* promoter operably linked to a DNA encoding at least one polypeptide from *Candida maltosa*. The gene linked to the first *Candida maltosa* promoter encodes cytochrome P450 monooxygenase and the gene linked to the second *Candida maltosa* promoter encodes cytochrome P450 reductase. More preferably, the first *Candida maltosa* promoter is PGK, the gene encoding cytochrome P450 monooxygenase is Alk1-A (D12475(SEQ ID NO:1)), Alk2-A (X55881(SEQ ID NO:2)), Alk3-A (X55881(SEQ ID NO:3)), Alk4-A (D12716 (SEQ ID NO:4)), Alk5-A (D12717(SEQ ID NO:5)), Alk6-A (D12718(SEQ ID NO:6)), Alk7 (D12719(SEQ ID NO:7)), and Alk8 (D12719(SEQ ID NO:8)).

Transformed *Candida maltosa* strains that have enhanced cytochrome P450 activity (including combined, simultaneous expression of alkane P450 monooxygenase, fatty acid monooxygenase and cytochrome P450-NADPH reductase expression) and/or gene disruptions in the β-oxidation pathway are described in U.S. Ser. No. 04/146,999. Based on growth and alkane utilization rates of the wild-type strain, further improvements in volumetric productivity (g product/L/hr) of either the P450 enhanced or β-blocked-strain would be required for an economical bioprocess. Hence, the combination of these two concepts provides a superior biocatalyst for the production of mono- and diterminal carboxylates from aliphatic substrates and gives the desired carboxylates in quantities and conversion efficiencies sufficient to be commercially viable.

One recombinant organism expresses enhanced alkane hydroxylating activity. The alkane hydroxylating activity is responsible for the hydroxylation of a terminal methyl group. The enhanced hydroxylating activity may be due to enhanced alkane monooxygenase, fatty acid monooxygenase or cytochrome P450 reductase separately or in various combinations. Additional enzymatic steps are required for its further oxidation to the carboxylate form. Two further oxidation steps, catalyzed by alcohol oxidase [Kemp et al., *Appl. Microbial. and Biotechnol.*, 28:370 (1988)] and alcohol dehydrogenase, lead to the corresponding carboxylate.

In *Candida maltosa*, amplification of at least one additional copy of cytochrome P450 monooxygenase and/or cytochrome P450 reductase would not be expected to lead to enhanced bioproduction of dicarboxylic acids in the presence of a functional β-oxidation pathway because the resulting fatty acids and/or dicarboxylic acids would be degraded as a carbon source for growth and biomass formation.

Another recombinant organism has gene disruptions in the β-oxidation pathway. The diploid yeast, *Candida maltosa*, grows on alkanes as a sole carbon source by deriving its carbon and energy through the β-oxidation pathway. This pathway is so efficient that wild-type strains normally do not produce di-carboxylic acids via ω-oxidation during growth on alkanes. The β-oxidation pathway was blocked in order to increase the metabolic flux to the ω-oxidation pathway and thereby increase the yield and selectivity of a bioprocess for conversion of alkanes to mono- and diterminal carboxylates.

A third recombinant organism has both enhanced alkane hydroxylating activity and gene disruptions in the β-oxidation pathway. The enhanced hydroxylating activity may be due to enhanced alkane monooxygenase, fatty acid monooxygenase or cytochrome P450 reductase separately or in various combinations.

Construction of Recombinant *Pichia pastoris*:

U.S. Ser. No. 04/146,999 relates to the genetic engineering of *Pichia pastoris* to achieve expression of active P450 systems derived from a heterologous source. Expression cassettes are constructed to include a promoter, such as, but not limited to, the strong, methanol-inducible promoter of alcohol oxidase I (AOX1) fused to the Alk1-A gene (or alternatively to the Alk3-A or P450 reductase genes) followed by a transcriptional terminator (such as from AOX1). The expression cassettes are subcloned into vectors containing suitable transformation markers, such as, but not limited to, HIS4, ARG4, SUC2 or the sh ble gene which encodes Zeocin resistance (Invitrogen, San Diego, Calif., USA). Sequential transformations of an appropriate strain of *Pichia pastoris* by established methods (U.S. Pat. No. 4,855,231) results in the integration of expression cassettes for genes into the *Pichia pastoris* genome. Transformants harboring multiple copies of the expression cassettes can be identified by a variety of methods such as, but not limited to, PCR and Southern blot analysis.

Also disclosed is engineering *Pichia pastoris* for expression of active P450 systems derived from a heterologous source by subcloning multiple expression cassettes onto one or two plasmids. For example, the expression cassettes for Alk1-A and Alk3-A genes may be subcloned on one plasmid and the expression cassette for P450 reductase gene may be subcloned on a second plasmid; or expression cassettes for Alk1-A and P450 reductase genes may be subcloned on one plasmid and the expression cassette for Alk3-A gene may be subcloned on a second plasmid; or the expression cassettes for Alk3-A and P450 reductase genes may be subcloned on one plasmid and the expression cassette for Alk1-A gene may be subcloned on a second plasmid; or the expression cassettes for Alk1-A and Alk3-A and P450 reductase genes may be subcloned on one plasmid. The plasmids are then used to sequentially or simultaneously transform a suitable *Pichia pastoris* host. Transformants harboring multiple copies of the expression cassettes can be identified by a variety of methods such as, but not limited to, PCR and Southern blot analysis.

Also disclosed is engineering *Pichia pastoris* for expression of active P450 systems derived from a heterologous source entails by subcloning expression cassettes for Alk1-A, Alk3-A and P450 reductase genes on to replicating plasmids, individually or in multiple copies as described above for the integration plasmids. The replicating plasmids are then used to sequentially or simultaneously transform a suitable *Pichia pastoris* host. Transformants harboring multiple copies of the expression cassettes can be identified by a variety of methods such as, but not limited to, PCR and Southern blot analysis.

Engineered *Pichia pastoris* cells containing multiple copies of expression cassettes for Alk1-A, Alk3-A and P450 reductase genes are grown to saturation in minimal medium containing glycerol (or glucose) as the carbon source, followed by induction of AOX1 promoter by methanol. This results in high level production of the P450 system components and high hydroxylating activity. Aliphatic substrate may be added before, at the beginning of, or any time during induction, and after a suitable time, the medium is analyzed for carboxylates as described above.

PCR Amplification of Genomic DNA from *Candida maltosa*:

Oligonucleotide primers are prepared based on sequences available from GenBank (National Center for Biotechnology Information, Bethesda, Md., USA) for the *Candida maltosa* IAM12247 cytochromes P450 Alk1-A and Alk3-A, and cytochrome P450 reductase genes, accession numbers D12475 (SEQ ID NO:1), X55881(SEQ ID NO:3), and D25327(SEQ ID NO:9), respectively. Appropriate, unique restriction sites are designed into the primers to allow convenient ligation into a cloning vector as well as construction of a gene expression cassette [See, for example, Sambrook et al, *Molecular Cloning: A Laboratory Manual*, Second Edition, Cold Spring Harbor Laboratory Press, (1989)]. In a similar manner, oligonucleotide primers are designed for the *Candida maltosa* IAM12247 URA3 gene. Using polymerase chain reaction (PCR) as described in U.S. Pat. No. 4,683,202 and/or U.S. Pat. No. 4,683,195, appropriate DNA sequences are amplified from genomic DNA obtained from *Candida maltosa* IAM12247 which corresponds to ATCC 90677. Similar protocols and appropriate primers would also allow PCR amplification of other *Candida maltosa* IAM12247 sequences available from GenBank including, but not limited to, cytochromes P450 Alk2-A (X55881(SEQ ID NO:2)), Alk4-A (D12716(SEQ ID NO:4)), Alk5-A (D12717(SEQ ID NO:5)), Alk6-A (D12718(SEQ ID NO:6)), Alk7 (D12719(SEQ ID NO:7)) and Alk8 (D12719(SEQ ID NO:8)).

Construction of Recombinant *Candida maltosa*—Chromosomal Integration:

The descriptions that follow use integrative transfer of the genes of interest in the transformed host.

The DNA fragments synthesized by PCR are sequentially inserted into a convenient cloning vector such as pUC18 or lambda Zap (Invitrogen, San Diego, Calif., USA) producing a vector which includes the gene cassette of the form Alk1-A/Alk3-A/P450 reductase/URA3/Alk1-A. After cloning of the vector containing the gene cassette in *E. coli*, the cassette fragment is linearized by cutting with appropriate restriction enzymes. *Candida maltosa* IAM12247 (corresponding to ATCC 28140) is transformed using techniques known in the art (Sambrook et al, supra) and transformants which have gained functional copies of the URA3 gene are selected by growth on minimal medium supplemented with histidine and adenine sulfate. Genomic DNA is isolated from the transformed strains using techniques known in the art. The genomic DNA is cut using appropriate restriction enzymes followed by probing using the Southern blot method. In this way, clones that have the maximum number of gene copies inserted into the chromosome are determined. Higher gene copy number generally results in higher levels of enzyme activity.

Also described is the sequential addition of the P450 system genes to the *Candida maltosa* chromosome. Insertion into the host genome of any cassette of the form X/URA3/X, where X=Alk1-A, Alk3-A, P450 reductase genes or other P450 system genes described above is accomplished by following a similar protocol of PCR amplification, cloning, linearization, transformation, minimal medium selection, and Southern blot screening to produce clones containing at least one additional copy of gene X for each original copy in the chromosome. Since different cytochrome P450 enzymes may have different substrate specificities, the insertion of the genes Alk1-A, Alk3-A and P450 reductase in any combination, or alternative insertions of one or more genes results in a set of biocatalysts useful for producing mono- or diterminal carboxylates from any appropriate substrate with a carbon number of 9 through 18.

The copy number of multiple genes is increased through successive integrative transformations, by inserting a recoverable marker gene along with the gene of interest during each transformation. The URA3 gene may be used repetitively. The ura3-genotype is regenerated by selective growth on 5-fluoroorotic acid after each transformation, allowing the same marker gene to be used for the next transformation. This process is repeated for each additional transformation. Alternatively, the his5 (GenBank Accession No. X17310) or ade1 (GenBank Accession No. D00855) marker genes are used as the marker gene. Since *Candida maltosa* strain ATCC 90677 is auxotropic for three different marker genes (URA3, HIS5 and ADE1), up to three genes of interest can be inserted before it is necessary to regenerate an auxotrophic mutation.

Construction of Recombinant *Candida maltosa*—Autonomous Replication:

An autonomously replicating sequence (ARS) may be added to the vector containing a cassette having the genes encoding a cytochrome P450 system. The host *Candida maltosa* is transformed with this construct. The vector is stably maintained in the host as a result of the ARS and selection pressure on a medium lacking uracil. As a result of the extra copies of the genes of interest carried by the vector, expression of active P450 systems is increased resulting in greater carboxylate production. The technique should not be considered limited by the use of genes Alk1-A, Alk3-A, P450 reductase and URA3 in this example. Any of the P450 system genes identified in this strain of *Candida maltosa* could be included alone or in combination in a replicative plasmid construct and transformed into *Candida maltosa* for the creation of a useful biocatalyst. Of particular use in the present invention are the genes Alk1-A, Alk3-A and P450 reductase. As a result of increased expression levels of appropriate P450 system genes, higher levels of carboxylate are produced.

Reaction Conditions for *Candida maltosa*:

Clones containing the highest levels of cytochrome P450 hydroxylating activity are grown for 2-3 days on suitable medium, optionally containing effective amounts of aliphatic substrate. At the end of this period, additional-substrate is added and the cells are incubated for another 1-2 days. Cells are removed and the supernatant is acidified resulting in the precipitation of the monoterminal and diterminal carboxylates. The precipitate and any dissolved carboxylates are extracted from the supernatant into methyl tertiary butyl ether (MTBE) and recovered in a substantially pure form after evaporation of the MTBE solvent.

Substrates for Reactions:

Suitable substrates for carboxylate production include straight chain hydrocarbons of carbon number $C_6$ to $C_{22}$, alone or in combination. Fatty acids with carbon number $C_6$ to $C_{22}$ also serve as substrates for diterminal carboxylate production. Furthermore, aliphatic hydrocarbons or fatty acids containing 1 or 2 double bonds in the carbon backbone can serve as substrates for the production of carboxylates where one or two additional terminal carboxylate groups appear in the products. Any of the straight chain compounds described above where one of the terminal carbons has been replaced by a phenyl group are also useful for carboxylate production.

Cell Strains and Growth Conditions:

*Candida maltosa* strains ATCC 90625 and ATCC 90677 (see ATCC Catalogue of Yeasts) are used for transformation and expression of alkane hydroxylating activity. *Pichia pastoris* strain GTS 115 is obtained from Invitrogen (San Diego, Calif., USA). These strains are routinely grown in YEPD medium (yeast extract, 10 g/L; peptone, 20 g/L; glucose, 20 g/L) at 30° C. with shaking at 250 rpm. Transformants of *Candida maltosa* ATCC 90677 with additional functional copies of the URA3 gene are selected by growth on minimal medium supplemented with histidine and adenine sulfate. The minimal medium is YNB (DIFCO Laboratories, Detroit Mich., USA), with amino acids+50 mg/L histidine and 20 mg/L adenosine sulfate+10 g/L glucose.

Examples 1-11, and the general methods related to them (paragraphs [0147], [0150], [0151], [0152], and [0153]), of U.S. Ser. No. 04/146,999 are incorporated by this reference in their entirety as a part hereof for all purposes.

EXAMPLES

The operation and effects of certain embodiments of the inventions hereof may be more fully appreciated from a series of examples, as described below. The embodiments on which these examples are based are representative only, and the selection of those embodiments to illustrate the invention does not indicate that materials, reactants, conditions, operating regimes and/or techniques not described in the examples are not suitable for use herein, or that subject matter not described in the examples is excluded from the scope of the appended claims and equivalents thereof.

Examples 1-11 illustrate hydrotreatment of different feeds to produce a hydrocarbon product comprising a linear alkane of $C_n$ chain length. Examples 9-11 include distillation of the hydrocarbon product to obtain at least one fraction of purified linear alkane of $C_n$ chain length. In Example 12, purified dodecane obtained in Example 9 is fermented to dodecanedioic acid by a transformed *Candida maltosa* strain SW81/82 identified as ATCC 74431. Example 13 demonstrates fermentation of dodecane obtained commercially and dodecane from Example 9 or 10.

The materials used were obtained as indicated in the examples. All commercial reagents were used as received. The following abbreviations are used: "C" is degrees Centigrade or Celsius; "%" is percent; "w/w" is weight for weight; "mL" is milliliter; "h" is hour(s); "rpm" is revolution per minute; "EtOH" is ethanol; "mg/g" is milligram per gram; "g/100 mL" is gram per 100 milliliter; "g" is gram(s); "NaOH" is sodium hydroxide; "w/v" is weight per volume; "v/v" is volume for volume; "w/w" is weight for weight; "mm" is millimeter; "mL/min" is milliliter per minute; "min" is minutes; "mM" is millimolar; "N" is normal; "μL" is microliter; "cc" is cubic centimeter(s); "sccm" is standard cubic centimeters per minute; and "OD" is outer diameter.

The feed and product compositions in the examples were measured using an Agilent Model 7890 Gas Chromatograph (Agilent Technologies, Santa Clara Calif.), equipped with a Flame Ionization Detector (FID) and a DB-1 Column (30 m×0.320 mm ID×0.25 um film thickness and manufactured by J&W Scientific, an Agilent Technologies Company, Santa Clara Calif.). The helium carrier gas (ultra high purity 99.99%, available from GTS Inc., Morrisville Pa.) flow rate was kept constant at 10 mL/min. An initial oven temperature of 75° C. and a temperature ramp of 7.5° C./min to 300° C. were employed in the method. The temperature was kept at 300° C. for an additional period of 5 minutes (total run time is 35 min). The injected sample was prepared in a 100:1 volumetric dilution in methylene chloride (reagent grade 99.9%, manufactured by EMD Chemicals Inc., an affiliate of Merck KGaA, Darmstadt, Germany). The injection volume was 1 μL. Several standard samples were prepared using $C_{10}$ through $C_{18}$ pure linear alkanes. It was determined that the weight percent (wt %) could be represented by GC area percent (area %) with an error of ±5%. Hence, GC area % obtained from the GC using the method described here was reported in all the examples as wt %.

GC results are given by indicating the alkane in shorthand notation. For example, "$C_{12}$" means the linear alkane containing 12 carbon atoms. "$C_{12}$ isomers" means the branched alkanes containing 12 carbon atoms. $C_{18+}$ means the total of alkanes containing greater than 18 carbons. $C_{8-}$ means the total of alkanes containing 3 to 7 carbons.

Catalyst Sulfiding Procedure

The following catalyst sulfiding procedure can be used when regeneration of the hydrotreating catalyst is necessary, for example after operations in which sulfur compounds were not present in the feed. Unsulfided hydrotreating catalysts may also be sulfided using this procedure.

A reactor consisting of ¾" (19 mm) OD 316L Stainless Steel tubing 14" (36 cm) long is used for sulfiding catalyst. The reactor is packed with alternating layers of 1 mm glass beads and PYREX wool at both ends, except in the middle, where catalyst (10 to 30 g) is packed. The reactor has 3 thermocouples measuring the gas inlet, gas outlet, and catalyst bed temperatures. The reactor is placed in the vertical tube furnace and the gas inlet and the gas outlet connections are established. The catalyst is allowed to dry overnight at 130° C. with a 200 sccm of nitrogen flow. After drying the catalyst, the oven temperature is increased at a rate of 0.5-1.0° C./minute and 20 sccm hydrogen sulfide (5% mixture in hydrogen) is added to the 200 sccm $N_2$ flow. Once the temperature reaches 190° C., the nitrogen flow is reduced to 100 sccm and the hydrogen sulfide flow is increased to 30 sccm. The temperature is held at 240° C. After 2 hours, the temperature is reduced slowly. Once the temperature is below 125° C., the hydrogen sulfide flow is stopped but the nitrogen flow is maintained at 100 sccm until reactor reaches room temperature (approx 25° C.). The reactor is removed from the furnace and is unloaded in a nitrogen purge box.

Catalyst Reduction Procedure

Similar equipment and set-up used for sulfiding catalyst is used for reducing the catalyst. The catalyst is dried overnight at 130° C. under a 200 sccm nitrogen flow. The reactor has 3 thermocouples measuring the gas inlet, gas outlet, and catalyst bed temperatures. The reactor is placed in the vertical tube furnace and the gas inlet and the gas outlet connections are established. The catalyst is allowed to dry overnight at 130° C. with a 200 sccm of nitrogen flow. After drying the catalyst, the oven temperature is increased at a rate of 0.5~1.0° C./minute and 20 sccm hydrogen gas (99.0% purity) is added to the 200 sccm $N_2$ flow. Once the temperature reaches 190° C., the nitrogen flow is reduced to 100 sccm and the hydrogen flow is increased to 30 sccm. The temperature is held at 240° C. unless noted otherwise. After 2 hours, the temperature is reduced slowly. Once the temperature is below 125° C., the hydrogen flow is stopped but the nitrogen flow is maintained at 100 sccm until reactor reaches room temperature (approx 25° C.). The reactor is removed from the furnace and is unloaded in a nitrogen purge box.

Table 1 shows the fatty acid chain lengths of the triglyceride and fatty acid sources (by weight percent) for the feeds used in most of the examples. The 50/50 mixture of soybean oil and chicken fat was prepared by mixing the two constituents in equal weights. The fatty acid chain lengths in Table 1 are given using lipid nomenclature of the form C:D, where C is the number of carbon atoms in the fatty acid and D is the number of double bonds in the fatty acid. For example, C18:1 refers to an 18 carbon chain with 1 unsaturated bond, C18:2 refers to an 18 carbon chain with 2 unsaturated bonds, and C18:3 refers to an 18 carbon chain with 3 unsaturated bonds.

In Table 1, $C_{18+}$ refers to fatty acids containing greater than 18 carbons. The values in Table 1 are representative of the triglyceride content of the indicated oils, which can vary from sample to sample. The lauric acid (dodecanoic acid) used in Example 11 contained about 98.9 weight percent $C_{12}$ alkane and about 1.1 weight percent $C_{14}$ alkane.

TABLE 1

Fatty acid chain lengths of triglyceride and fatty acid sources by weight percent.

|  | Coconut Oil | Palm Kernel Oil | Palm Oil | Soybean Oil | Chicken Fat |
|---|---|---|---|---|---|
| C6:0 | 0.5 | | | | |
| C8:0 | 7.5 | 3.5 | | | |
| C10:0 | 5.8 | 3.4 | | | |
| C12:0 | 45.6 | 46.2 | | | |
| C14:0 | 18.4 | 17.0 | 1.0 | | 0.6 |
| C16:0 | 9.2 | 8.8 | 45.4 | 10.2 | 27.5 |
| C16:1 | | | | | 3.0 |
| C18:0 | 3.5 | 3.0 | 4.3 | 4.4 | 6.0 |
| C18:1 | 6.2 | 15.0 | 38.8 | 23.3 | 40.3 |
| C18:2 | 2.8 | 3.1 | 9.9 | 53.2 | 6.4 |
| C18:3 | | | | 6.5 | |
| $C_{18+}$ | 0.5 | | 0.6 | 2.4 | 1.8 |
| Free Acids | | | | | 13.2 |
| Total | 100.0 | 100.0 | 100.0 | 100.0 | 100.0 |

Example 1

Hydrotreating of Refined Coconut Oil

Refined coconut oil, (50 g, obtained from Spectrum Chemicals of Gardena Calif.) and alumina-supported pre-sulfided cobalt/nickel/molybdenum tri-metallic hydrotreating catalyst (5 g, CRI DC2318, commercially available from Criterion Catalysts and Technologies, Houston Tex.) were placed in a 210 cc agitated pressure reactor. The vessel was leaked check with nitrogen. The headspace of the reactor was purged with nitrogen 10 times by pressurizing to 90 psig (722 kPa) and depressurizing to 0 psig (101 kPa). The reactor was then purged with high purity hydrogen (99.9% min., commercially available from Air Products, Allentown Pa.) five times, and pressurized to 1000 psig (7000 kPa) with hydrogen. The reactor and its contents were agitated and heated to 325° C. (617° F.). The hydrogen pressure was increased to 2000 psig (13,900 kPa), and maintained there for 5 hours. The headspace was filled with fresh hydrogen to 1500-1700 psig (11,800 kPa) if the pressure dropped below 1000 psig (7000 kPa).

The reactor contents were then cooled to below 50° C. (122° F.), the headspace was vented, and the contents were discharged to a glass bottle. The contents were weighed. IR and $^1$H NMR analysis showed no evidence of mono-, di- and triglycerides. The reaction products were analyzed by GC-FID to obtain the following linear hydrocarbon distribution by weight: $C_{18}$=8%, $C_{17}$=1%, $C_{16}$=8%, $C_{15}$=1%, $C_{14}$=15%, $C_{13}$=2%, $C_{12}$=40%, $C_{11}$32 4%, $C_{10}$=6%, $C_9$=1%, $C_8$=10%, $C_{8-}$=1%. The reaction products also contained about 3% other compounds, mainly the branched isomers of $C_8$ through $C_{18}$ alkanes.

Example 2

Hydrotreating of Palm Oil

The process of Example 1 was repeated using the same equipment, pressure, temperature, and catalyst (5 g), except palm oil (50 g, manufactured by T.I. International Ghana Ltd. of Accra, Ghana) was used. The reaction products were analyzed by GC-FID to obtain the following linear hydrocarbon distribution by weight: $C_{18+}$=0.5%, $C_{18}$=46.5%, $C_{17}$=5%, $C_{16}$=43%, $C_{15}$=4%, $C_{14}$=1%.

Example 3

Hydrotreating of Chicken Fat

The process of Example 1 was repeated using the same equipment, pressure, temperature, and catalyst (5 g), except chicken fat (50 g, obtained from Perdue Farms of Salisbury Md.) was used. The reaction products were analyzed by GC-FID to obtain the following linear hydrocarbon distribution by weight: $C_{18+}$=1%, $C_{18}$=60%, $C_{17}$=7%, $C_{16}$=28%, $C_{15}$=3%, $C_{14}$=1%.

Example 4

Hydrotreating of 50/50 Chicken Fat/Soybean Oil

The process of Example 1 was repeated using the same equipment, pressure, temperature, and catalyst (5 g), except a 50:50 chicken fat to soybean oil mixture (50 g, mixed in-house with chicken fat and soybean oil obtained from Perdue Farms of Salisbury Md.) was used. The reaction products were analyzed by GC-FID to obtain the following linear hydrocarbon distribution by weight: $C_{18+}$=2.1%, $C_{18}$=69.6%, $C_{17}$=7.2%, $C_{16}$=18.5%, $C_{15}$=1.9%, $C_{14}$=0.5%, $C_{13}$=0.1%, $C_{12}$=0.1%.

Example 5

Hydrotreating of Palm Kernel Oil

The process of Example 1 was repeated using the same pressure and temperature except 10 g of the same CRI DC-2318 catalyst and palm kernel oil (100 g, obtained from Columbus Foods Company of Des Plains Ill. via their web-based division soaperschoice.com) were used in a larger (400 cc) agitated pressure reactor. The reaction products were analyzed by GC-FID to obtain the following linear hydrocarbon distribution by weight: $C_{18+}$=0.4%, $C_{18}$=19.3%, $C_{17}$=2.5%, $C_{16}$=7.9%, $C_{15}$=1.1%, $C_{14}$=15.0%, $C_{13}$=2.0%, $C_{12}$=40.2%, $C_{11}$=4.6%, $C_{10}$=3%, $C_9$=0.4%, $C_8$=3.2%, $C_{8-}$=0.4%.

Example 6

Hydrotreating of Soybean Oil

The process of Example 1 was repeated using the same equipment, pressure, temperature, and catalyst (5 g), except soybean oil (50 g, obtained from Sigma-Aldrich of St. Louis, Mo.) was used. IR and $^1$H NMR analysis of the discharged reactor contents (51 g) showed no evidence of mono-, di- and triglycerides. The reaction products were analyzed by GC-FID to obtain the following linear hydrocarbon distribution by weight: $C_{18+}$=1%, $C_{18}$=81%, $C_{17}$=6%, $C_{16}$=11.5%, $C_{15}$=0.5%. The $C_{18}$:$C_{17}$ ratio is greater than 13:1 and the $C_{16}$:$C_{15}$ ratio is greater than 20:1.

Example 7

Hydrotreating of Refined Soybean Oil

The process of Example 1 was repeated using the same equipment, pressure, temperature, and catalyst (5 g), except a refined, bleached, and deodorized soybean oil sample (50 g, obtained from Perdue Farms, Salisbury Md.) was used. The reaction products were analyzed by GC-FID to obtain the following linear hydrocarbon distribution by weight: $C_{18+}=$ 0.5%, $C_{18}=79\%$, $C_{17}=8\%$, $C_{16}=11.3\%$, $C_{15}=1.2\%$. The $C_{18}$:$C_{17}$ ratio is almost 10, and the $C_{16}$:$C_{15}$ ratio is greater than 9.

Example 8

Hydrotreating of Stearic Acid

The process of Example 1 was repeated using the same equipment, pressure, temperature, and catalyst (5 g), except stearic acid (50 g, from VWR, West Chester, Pa.) was used. The reaction products were analyzed by GC-FID to obtain the following linear hydrocarbon distribution by weight: $C_{18+}=$ 0.7%, $C_{18}=90.4\%$, $C_{17}=8.4\%$, $C_{16}=0.5\%$. The $C_{18}$:$C_{17}$ ratio is approximately 10.8.

Example 9

Hydrotreating of Crude Coconut Oil and Distillation of the Hydrocarbon Product

The process of Example 1 was repeated using a larger (400 cc) agitated pressure reactor at twice the recipe, otherwise using the same pressure, temperature, catalyst, and crude coconut oil (100 g, from Spectrum Chemicals) The reaction products were analyzed by GC-FID to obtain the following linear hydrocarbon distribution by weight: $C_{18+}=0.5\%$, $C_{18}=8.9\%$, $C_{17}=1.5\%$, $C_{16}=8.7\%$, $C_{15}=1.0\%$, $C_{14}=16.9\%$, $C_{13}=2.3\%$, $C_{12}=42.2\%$, $C_{11}=4.9\%$, $C_{10}=5.3\%$, $C_9=0.5\%$, $C_8=6.7\%$, $C_{8-}=0.6\%$.

Example 9 was repeated three additional times and the samples were processed to separate the wet catalyst and the water layer to obtain 360 g of combined hydrocarbon sample, which was analyzed by GC-FID to obtain of the following linear hydrocarbon distribution by weight: $C_{18+}=0.6\%$, $C_{18}=8.9\%$, $C_{17}=1.8\%$, $C_{16}=8.6\%$, $C_{15}=1.5\%$, $C_{14}=16.7$, $C_{13}=2.5$, $C_{12}=42.4\%$, $C_{11}=4.6$, $C_{10}=5.1$, $C_9=0.6$, $C_8=6.2\%$, $C_{8-}=0.5\%$.

Of the combined hydrocarbon sample, 290 g was vacuum-distilled at 50 torr (absolute) pressure in a 10-plate 1" internal diameter (I.D.) laboratory Oldershaw column using a 1-L round bottom flask as reboiler to obtain a 51 g foreshot (having the following linear hydrocarbon distribution by weight: $C_{12}=8.7\%$, $C_{11}=22.3\%$, $C_{10}=28.0\%$, $C_9=3.2\%$, $C_8=35.0\%$, $C_{8-}=2.8\%$), an 89 g heart-cut (having the following linear hydrocarbon distribution by weight: $C_{14}=0.1\%$, $C_{13}=0.2\%$, $C_{12}=97.6\%$, $C_{11}=2.1\%$), and a 141 g bottoms fraction remaining in the reboiler (having the following linear hydrocarbon distribution by weight: $C_{18+}=1.3\%$, $C_{18}=19.6\%$, $C_{17}=3.0\%$, $C_{16}=17.6\%$, $C_{15}=3.4\%$, $C_{14}=35.0\%$, $C_{13}=4.0\%$, and $C_{12}=16.1\%$). The reflux ratio was maintained at 4:1 during the distillation. During the foreshot collection, the reboiler temperature varied between 133° C. and 148° C. and the head temperature varied between 50° C. and 127° C. During the heartcut collection, the reboiler temperature varied between 148° C. and 166° C. and the head temperature varied between 127° C. and 128° C. A portion of this heartcut was used in Example 12 for fermentation to the linear $C_{12}$ dicarboxylic acid.

If desired, using appropriate distillation conditions, the bottoms fraction could be distilled to obtain another alkane fraction, for example a $C_{14}$, $C_{16}$, or $C_{18}$ fraction, of sufficient purity to be fermented to the corresponding dicarboxylic acid. Likewise, using appropriate distillation conditions the foreshot could be distilled to obtain a $C_{10}$ alkane fraction of sufficient purity to be fermented to the corresponding dicarboxylic acid.

An additional laboratory distillation of the heartcut containing 97.6% linear $C_{12}$ alkane was performed to demonstrate further refining of the sample through distillation. A portion (2400 g) of the 3200 g heartcut sample from above was charged to a 5-L flask with a 5-tray Oldershaw column and a reflux splitter. Distillate was taken overhead at a 20:1 reflux ratio and a 50 mm Hg (absolute) head pressure until 400 g of foreshot was collected. The final reboiler temperature was 129.7° C. and the final head temperature was 117.7° C. At the end of the distillation, the 5 L flask contained 1975 g of colorless liquid which was analyzed by GC-FID to obtain the following hydrocarbon distribution by weight: linear $C_{12}=99.0\%$, branched $C_{12}$ isomers 1.0%.

Example 10

Hydrotreating of Refined Coconut Oil and Distillation of the Hydrocarbon Product Solid refined coconut oil (1000 g, obtained from Spectrum Chemicals of Gardena, Calif.) and alumina-supported pre-sulfided cobalt/nickel/molybdenum tri-metallic hydrotreating catalyst (75 g, CRI DC2318, commercially available from Criterion Catalysts and Technologies, Houston Tex.) were placed in a 1-gallon agitated pressure reactor. The agitation at 1,000 rpm by a turbine type impeller created a suction at the blades of the agitator which allowed the circulation of hydrogen from the headspace through the shaft of the agitator, bubbling in the agitated liquid reaction mixture. The reactor was first heated to 50° C. to melt the coconut oil with slow agitation at 100 rpm. The vessel was leaked check with nitrogen. The headspace of the reactor was purged with nitrogen 10 times by pressurizing to 90 psig (722 kPa) and depressurizing to 2 psig (115 kPa). The reactor was then purged with high purity hydrogen (99.9% min., commercially available from Air Products, Allentown Pa.) five times, and pressurized to 750 psig (7000 kPa) with hydrogen. The reactor and its contents were slowly pressurized to 2,000 psig (13,900 kPa) and heated to 325° C. (617° F.) in steps while being agitated. The reactor contents were kept at 325° C. (617° F.) and 2000 psig (13,900 kPa) for a total of 5 hours. The headspace was filled during this time with additional hydrogen if the pressure went below 2,000 psig.

The reactor contents were then cooled to below 50° C. (122° F.), the headspace was vented, and the contents were discharged to a glass jar. The contents were weighed and found to be 1027 g, including the catalyst and the water produced. The reaction products were analyzed by GC-FID to obtain the following linear hydrocarbon distribution by weight: $C_{18+}=0.3\%$, $C_{18}=8.8\%$, $C_{17}=1.6\%$, $C_{16}=7.7\%$, $C_{15}=1.4\%$, $C_{14}=16.3\%$, $C_{13}=2.6\%$, $C_{12}=39.5\%$, $C_{12}$ isomers=1.5%, $C_{11}=6.1\%$, $C_{10}=5.4\%$, $C_9=0.8\%$, $C_8=6.5\%$, and $C_{8-}=1.5\%$.

The experiment was repeated 11 more times and the products of all the runs were combined (after separating for each run the water layer and the wet catalyst) to obtain a combined hydrocarbon sample of 9277 g. A GC-FID analysis of the combined hydrocarbon sample gave the following linear hydrocarbon distribution by weight: $C_{18+}=0.4\%$, $C_{18}=10.0\%$, $C_{17}=1.6\%$, $C_{16}=8.1\%$, $C_{15}=1.4\%$, $C_{14}=16.3\%$, $C_{13}=2.6\%$, $C_{12}=39.0\%$, $C_{12}$ isomers=1.5%, $C_{11}=6.0\%$, $C_{10}=5.0\%$, $C_9=0.7\%$, $C_8=5.9\%$, and $C_{8-}=1.5\%$.

A portion (9150 g) of the combined hydrocarbon product from above was vacuum-distilled at 50 ton (absolute) pressure in a 25-plate 2" I.D., silver coated, vacuum jacketed glass laboratory Oldershaw column using a 22-L round bottom flask as reboiler to obtain a foreshot (2180 g having the following linear hydrocarbon distribution by weight: $C_{12}$=17.2%, $C_{12}$ isomers=3.4%, $C_{11}$=24.3%, $C_{10}$=21.0%, $C_9$=3.1%, $C_8$=24.8%, $C_{8-}$=6.2%), a heart-cut (3200 g having the following linear hydrocarbon distribution by weight: $C_{12}$=97.4%, $C_{12}$ isomers=2.0%, $C_{11}$=0.6%), and a bottoms fraction remaining in the reboiler (3750 g having the following linear hydrocarbon distribution by weight:$C_{18+}$=1.0%, $C_{18}$=25.1%, $C_{17}$=3.9%, $C_{16}$=20.2%, $C_{15}$=3.4%, $C_{14}$=42.2%, $C_{13}$=4.1%, and $C_{12}$=0.1%). The reflux ratio was maintained at 10:1 during the distillation. During the foreshot collection, the reboiler temperature varied between 135° C. and 150° C. and the head temperature varied between 50° C. and 124° C. During the heartcut collection, the reboiler temperature varied between 150° C. and 177° C. and the head temperature varied between 124° C. and 124.5° C. The combined weight of the foreshot, heartcut, and bottoms fractions from the distillation was 9130 g. The heart-cut fraction was of sufficient purity to be suitable for fermentation to the linear $C_{12}$ dicarboxylic acid.

TABLE 2

First Distillation: Compositions of Feed, Foreshot, Heartcut, and Bottoms Fractions (Example 10).

| Alkane | Feed to Distillation (g) | Foreshot (g) | Heart cut (g) | Bottoms (g) |
|---|---|---|---|---|
| $C_{8-}$ | 1.5 | 6.2 | | |
| $C_8$ | 5.9 | 24.8 | | |
| $C_9$ | 0.7 | 3.1 | | |
| $C_{10}$ | 5.0 | 21.0 | | |
| $C_{11}$ | 6.0 | 24.3 | 0.6 | |
| $C_{12}$ isom* | 1.5 | 3.4 | 2.0 | |
| $C_{12}$ | 39.0 | 17.2 | 97.4 | 0.1 |
| $C_{13}$ | 2.6 | | | 4.1 |
| $C_{14}$ | 16.3 | | | 42.2 |
| $C_{15}$ | 1.4 | | | 3.4 |
| $C_{16}$ | 8.1 | | | 20.2 |
| $C_{17}$ | 1.6 | | | 3.9 |
| $C_{18}$ | 10.0 | | | 25.1 |
| $C_{18+}$ | 0.4 | | | 1.0 |

*"$C_{12}$ isom" refers to branched isomers of dodecane.

In a subsequent (second) distillation in the same 2" I.D. and 25-plate glass Oldershaw column described above, the remaining bottoms fraction (3750 g), was distilled further at 20 torr (absolute) pressure to obtain a foreshot (426 g having the following linear hydrocarbon distribution by weight: $C_{14}$=57.5%, $C_{14}$ isomers=10.8%, $C_{13}$=31.1%, and $C_{12}$=0.6%), a heart-cut (1066 g having the following linear paraffin distribution by weight: $C_{15}$=0.2%, $C_{14}$=98.6%, $C_{14}$ isomers=1.1%, and $C_{13}$=0.1%), and a bottoms fraction (2228 g having the following linear hydrocarbon distribution by weight:$C_{18+}$=2.0%, $C_{18}$=46.3%, $C_{17}$=7.3%, $C_{16}$=37.0%, $C_{15}$=6.1%, and $C_{14}$=1.3%). The reflux ratio was maintained at 10:1 during the distillation. During the foreshot collection, the reboiler temperature varied between 160° C. and 171° C. and the head temperature varied between 105° C. and 136° C. During the heartcut collection, the reboiler temperature varied between 171° C. and 192° C. and the head temperature varied between 136° C. and 137° C. The combined weight of the foreshot, heartcut, and bottoms fractions from the distillation was 3720 g. The heart-cut fraction is believed to be of sufficient purity that it would be suitable for fermentation to the linear $C_{14}$ dicarboxylic acid.

TABLE 3

Second Distillation: Compositions of Feed, Foreshot, Heartcut, and Bottoms Fractions (Example 10).

| Alkane | Feed to Distillation (g) | Foreshot (g) | Heart cut (g) | Bottoms (g) |
|---|---|---|---|---|
| $C_{12}$ | 0.1 | 0.6 | | |
| $C_{13}$ | 4.1 | 31.1 | 0.1 | |
| $C_{14}$ isom* | 1.6 | 10.8 | 1.1 | |
| $C_{14}$ | 40.6 | 57.5 | 98.6 | 1.3 |
| $C_{15}$ | 3.4 | | 0.2 | 6.1 |
| $C_{16}$ | 20.2 | | | 37.0 |
| $C_{17}$ | 3.9 | | | 7.3 |
| $C_{18}$ | 25.1 | | | 46.3 |
| $C_{18+}$ | 1.0 | | | 2.0 |

*"$C_{14}$ isom" refers to branched isomers of dodecane.

Example 11

Hydrotreating of Dodecanoic Acid and Distillation of the Hydrocarbon Product

Dodecanoic acid, (1000 g, 98% pure, solid, obtained from Aldrich Chemicals) and alumina-supported pre-sulfided cobalt/nickel/molybdenum tri-metallic hydrotreating catalyst (75 g, CRI DC2318, commercially available from Criterion Catalysts and Technologies, Houston Tex.) were placed in a 1-gallon agitated pressure reactor. The agitation at 1,000 rpm by a turbine type impeller created a suction at the blades of the agitator which allowed the circulation of hydrogen from the headspace through the shaft of the agitator, bubbling in the agitated liquid reaction mixture. The reactor was first heated to 50° C. to melt the dodecanoic acid while agitating slowly at 100 rpm. The vessel was leaked check with nitrogen. The headspace of the reactor was purged with nitrogen 10 times by pressurizing to 90 psig (722 kPa) and depressurizing to 2 psig (115 kPa). The reactor was then purged with high purity hydrogen (99.9% min., commercially available from Air Products, Allentown Pa.) five times, and pressurized to 750 psig (7000 kPa) with hydrogen. The reactor and its contents were slowly pressurized to 2,000 psig (13,900 kPa) and heated to 325° C. (617° F.) in steps while being agitated. The reactor contents were kept at 325° C. (617° F.) and 2000 psig (13,900 kPa) for a total of 5 hours.

The experiment above was repeated twice and the products of the runs were combined to obtain 2130 g of gross reaction mixture. After separating the water layer and the wet catalyst (with some hydrocarbon loss), a combined hydrocarbon sample of 1602 g was obtained. A GC-FID analysis of this combined sample gave the following linear hydrocarbon distribution by weight: $C_{14}$=0.5%, $C_{13}$=0.6%, $C_{12}$=85.1%, $C_{12}$ isomers=3.0%, $C_{11}$=10.4%, $C_{11-}$=0.4%.

The combined reaction product from above was vacuum distilled. Reaction product (1590 g) was charged to a 5-liter flask with a 5-tray Oldershaw column and a reflux splitter. The starting material was yellow in color. Distillate was taken overhead at a 20:1 reflux ratio, and a 50 mm Hg absolute head pressure until 274.5 g of foreshot was collected. A GC-FID analysis of the foreshot gave the following linear hydrocarbon distribution by weight: $C_{10}$=0.9%, $C_{11}$ isomers=2.0%, $C_{11}$=42.4%, $C_{12}$ isomers=4.8% and $C_{12}$=49.9%. Final pot temperature was 128.6° C. and the final head temperature was 121.6° C.

The foreshot receiver was replaced and the distillation continued. A colorless product cut was taken overhead at a 2.5:1 reflux ratio and a 50 mm Hg absolute head pressure.

Final head temperature was 126.3° C. The pot contained 79.6 g of gold colored liquid (GC-FID analysis gave the following linear hydrocarbon distribution by weight: $C_{12}$=46.7%, $C_{12+}$=53.3%). After emptying the pot, the product cut was recharged to the pot and an additional 183.7 g of foreshot (GC-FID analysis gave the following linear hydrocarbon distribution by weight: $C_{11}$=13.1%, $C_{12}$ isomers=5.5%, $C_{12}$=81.4%) was taken overhead at a 20:1 reflux ratio and a 50 mm Hg absolute pressure. The final head temperature was 123.5° C. Final product was collected from the pot (GC-FID analysis gave the following linear hydrocarbon distribution by weight: 1028.3g, $C_{11}$=0.6%, $C_{12}$ isomers=1.7%, and $C_{12}$=97.7%).

Example 12

Fermentation of Dodecane Obtained in Example 9 to Dodecanedioic Acid

Strain SW 81/82, ATCC 74431, is genetically modified *Candida maltosa* yeast. This species is naturally capable of $C_{12}$-$C_{16}$ alkane oxidation. Typically the alkane is oxidized through the corresponding alcohol and aldehyde. Upon reaching the corresponding acid, the acid is fed into central metabolism via beta oxidation. In this genetically modified strain, beta oxidation has been blocked, resulting in accumulation of the corresponding diacid. The SW 81/82 used in this fermentation example was produced as disclosed in U.S. Ser. No. 04/146,999.

Dodecanedioic acid was produced in a two-stage fermentation using strain SW 81/82. In the first stage, cell production stage, yeast cells grew on glucose and accumulated biomass. In the second stage, diacid production stage, yeast cells were maintained with glycerol additions and glucose was absent. Dodecane was added at this stage and the yeast converted it to dodecanedioic acid. Oxygenation is critical in both stages and the medium was stirred vigorously and continuously. The medium pH is also critical and was maintained in the neutral range. To aid in pH control a combination of bromothymol blue/cresol red, colorimetric pH indicators, was used and maintained at the green to sky blue transition point, ~pH 7.6.

The following composition was used for first-stage medium, per liter: 20 mL Difco Yeast Nitrogen Base (available from VWR), West Chester Pa.), 24 g glucose (available from VWR), 0.4 g peptone (available from VWR), 24 g HEPES (available from VWR), and 0.4 g yeast extract (available from VWR). The medium pH was adjusted to approximately 6.5 and filter sterilized. In the second stage the medium composition, per liter, was 2 g Difco Yeast Nitrogen Base, 8 mL glycerol (available from VWR), 2 g peptone, 24 g HEPES, 0.4 g yeast extract, 2 mL Cresol red (available from VWR) indicator solution, and 2 mL Bromothymol blue (available from VWR) indicator solution. The medium was adjusted to approximately pH 7.8 and filter sterilized. Glucose concentrations during the fermentation were measured using Uriscan glucose strips (YD Diagnostics, Seoul, Korea).

Two 500 mL flasks containing 100 mL of first stage medium were placed on magnetic stirrers and the stir rate was set to approximately 1200 rpm. Flasks were inoculated from frozen stock of SW 81/82 to an initial optical density of approximately 0.12 at 600 nm. After 24 hours growth at room temperature cultures had reached an optical density of 10.4 and 6.6, respectively, for replicate flasks 1 and 2. Medium pH had fallen to approximately 4 after 29 hours of growth. More than 20 g/L glucose remained in the medium at 29 hours. After an additional 48 h glucose concentrations had fallen to less than 1 g/L. At this point cells were prepared for stage two of the fermentation, the dodecanedioic acid production phase. Yeast cells were collected by centrifugation, removed from stage-one medium and suspended in stage-two medium. Both stage-two flasks contained 100 mL of stage-two medium and 2 mL of dodecane (obtained from the heartcut fraction of Example 9) in addition to the yeast cells. The stirred stage-two flasks were incubated at room temperature, approximately 24° C. The pH was periodically readjusted to approximately pH 7.8 by manual addition of 1N NaOH. After approximately 48 h of stage-two incubation, the fermentations were stopped.

Sodium hydroxide was added to flasks 1 and 2 to bring the pH to approximately 8.4. Cells were separated from the alkaline supernatant by centrifugation. One set of samples was processed for liquid chromatographic analysis. Another set was processed for crude acid insolubles (mostly dodecanedioic acid) isolation. Duplicate samples of crude isolate were obtained by first adding 1N HCl to lower the pH of duplicate 5 mL samples of cell-free supernatant to approximately pH 3. Precipitate was allowed to form for approximately 10 minutes. The precipitate was separated from the acidified supernatant by centrifugation and washed twice with 0.01 N HCl. The washed solids were placed at 30° C. to dry for 48 hours. Dried solids were dissolved in 100% ethanol and any insoluble material was separated from the ethanol solution by centrifugation. The ethanol solution was dried at 30° C. for 48 hours to yield a white crystalline ethanol-soluble solid characteristic of dodecanedioic acid. Approximately 267 mg/L of acid insolubles were produced from each of the two replicate flasks.

Samples were processed for liquid chromatographic analysis to detect dodecanedioic acid. Fermentation samples were adjusted to pH 12 with 30% NaOH and extracted with hexane to remove dodecane. The aqueous layer was injected on a liquid chromatograph using a Zorbax C18 (3 micron packing) column, 250×4.6 mm. Acetonitrile/water with 1% TFA was used as the mobile phase. The mobile phase gradient was 5% acetonitrile to 100% acetonitrile in 10 minutes and hold at 100% acetonitrile for an additional 5 min. Mobile phase flow was 1 ml/min. Column temperature was 40° C. A single point standard was used for calibration. Identification was by retention time against the standard Liquid chromatographic analysis gave estimates of 307 mg/L and 354 mg/L of dodecanedioic acid from the respective replicate fermentation flasks.

Examples 13A, 13B and 13C

Fermentation of Commercial Dodecane (Example 13A) and Dodecane Obtained Experimentally (Examples 13B and 13C) to Dodecanedioic Acid Example 13A was performed with purchased dodecane unlike Examples 13B and 13C, which were performed with dodecane obtained by a process hereof. A different fermentation protocol was used in Examples 13A~13C than in Example 12 although the first and second stage media were the same as in Example 12.

A 40 mL sterile agar layer containing 20 g/L glucose, 4.8 g/L HEPES (pH 7.1), 20 g/L peptone and 10 g/L yeast extract was made in the bottom of nine sterile 500 mL bottles. A lawn of strain SW 81/82 *Candida maltosa* was established on the agar surface by 30° C. overnight incubation. At the start of the first dodecanedioic acid (DDDA) production cycle 5 mL of sterile 0.01 M PBS (phosphate buffered saline, pH 7.2)+0.5 mL of commercial dodecane (Sigma-Aldrich) was added to triplicate yeast lawn-containing bottles. In addition 5 mL of sterile 0.01 M PBS+0.5 mL of dodecane (obtained from Example 9 or 10) was added to a second set of triplicate yeast lawn-containing bottles. Also, 5 mL of sterile 0.01 M PBS+ 0.5 mL of dodecane (obtained from Example 9 or 10) was added to a third set of triplicate yeast lawn-containing bottles.

Bottles were shaken at 200 rpm at room temperature for the first production cycle. After 4 days, the cells and liquid phases were harvested and refrigerated at 4° C. The second production cycle was then started.

For the second DDDA production cycle, 5 mL of sterile 0.01 M PBS+0.5 mL of commercial dodecane (Sigma-Aldrich) was added to triplicate yeast lawn-containing bottles. In addition 5 mL of sterile 0.01 M PBS+0.5 mL of dodecane (obtained from Example 9 or 10) was added to a second set of triplicate yeast lawn-containing bottles. Also, 5 mL of sterile 0.01 M PBS+0.5 mL of dodecane (obtained from Example 9 or 10) was added to a third set of triplicate yeast lawn-containing bottles. Bottles were shaken at 200 rpm at room temperature. After 2 days the cells and liquid phases were harvested.

Liquid and cell phases from both production cycles were extracted with decane to recover any dodecane remaining. Agar remaining in the bottles was also extracted with decane to recover any dodecane remaining. The pH in liquid and cell phases from both cycles was raised to a pH of 9-9.5 to dissolve the dodecanedioic acid. Alkaline cell suspensions were centrifuged to remove cells. Agar remaining in the bottom of the bottles also received an alkaline wash to dissolve dodecanedioic acid. Alkaline liquid phases were then adjusted to a pH of approximately 2 and solids were allowed to precipitate overnight at 4° C.

Precipitated solids and collected cells were dried overnight at 60° C. All dried solids were extracted with acidified (HCl) isopropanol to extract dodecanedioic acid. Extracts were dried at room temperature under a nitrogen flow. Sample fractions were prepared for analysis by gas chromatography-mass spectrometry.

Dodecanedioic acid in the samples was analyzed using derivatization with BSTFA+1% TMS followed by injection onto a Hewlett-Packard 5890 gas chromatograph with a DB5 30 m×0.25 mm id, 0.25 film column. In performing chromatography, a temperature program of 40° C. for 1 minute, 7° C./minute ramp to 300° C. with a final hold for 5 minutes was used. Compounds were detected on a HP5971 Mass Spectrometer. Molecular weights from 18 to 500 mass units were scanned. Dodecanedioic acid retention time was confirmed using standards made with commercial dodecanedioic acid. The mass spectrometer fragmentation pattern confirmed that the material in the monitored sample peak was dodecanedioic acid. An internal standard, ethylene glycol diethyl ether, relative response factor calibration was used to estimate the amount of dodecanedioic acid present in the samples.

Mean dodecanedioic acid (DDDA) concentrations produced in fermentation vessels for the three samples of dodecane converted were 30.7 mg/L, 30.0 mg/L and 25.6 mg/L for the Sigma-Aldrich dodecane (Example 13A), and for the dodecane samples obtained from Example 9 or 10 (Examples 13B and 13C), respectively. Dodecane source did not appear to have any significant impact on molar dodecanedioic acid yield. The mean values were not significantly different at the p=0.05 level in a two tailed t-test. Yields attained under manual, lab-scale conditions with less than optimal process control may differ from those attained using automated process control at full fermentation-scale.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage,
(a) amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value; and
(b) use of the indefinite article "a" or "an" with respect to a statement or description of the presence of an element or feature of this invention, does not limit the presence of the element or feature to one in number.

What is claimed is:

1. A process of making a linear dicarboxylic acid of $C_n$ chain length, comprising:
   (a) providing a feed that is a renewable resource;
   (b) contacting the feed with a catalyst in the presence of hydrogen to produce a hydrocarbon product having at least a 10:1 ratio of even-numbered alkanes to odd-numbered alkanes and comprising a linear alkane of $C_n$ chain length; and
   (c) fermenting at least a portion of the linear alkane of $C_n$ chain length to a linear dicarboxylic acid of $C_n$ chain length;
   wherein n=10, 12, 14, 16 or 18; and
   wherein the catalyst comprises alumina-supported, pre-sulfided cobalt, nickel and molybdenum.

2. The process of claim 1, wherein the feed is contacted with the catalyst in the presence of hydrogen at a temperature of about 250° C. to about 425° C. and at a pressure of about 500 psig to about 2500 psig.

3. The process of claim 1, wherein the feed comprises
   (a) an oil derived from plants and/or animals and comprising one or more free fatty acids and/or one or more triglycerides, the oil comprising at least about 5 mole % of a linear fatty acid of $C_n$ chain length, and/or at least about 5 mole % of a triglyceride derived from a linear fatty acid of $C_n$ chain length;
   (b) an alkyl ester of a fatty acid derived from triglycerides, the ester comprising at least about 5 mole % of an ester of a linear fatty acid of $C_n$ chain length; or
   (c) a mixture thereof.

4. The process of claim 3, wherein the feed comprises an oil comprising at least about 5 mole % of a linear fatty acid of $C_n$ chain length.

5. The process of claim 3, wherein the fatty acid is selected from the group consisting of lauric acid, myristic acid, palmitic acid, and a combination of these.

6. The process of claim 3, wherein the feed comprises a vegetable oil selected from the group consisting of coconut oil, palm kernel oil, palm oil, rapeseed oil, canola oil, soybean oil, cottonseed oil, and a combination of these.

7. The process of claim 3, wherein the feed comprises poultry fat, yellow grease, tallow, or a combination of these.

8. The process of claim 3, wherein the feed comprises an ester of a fatty acid derived from triglycerides, the ester comprising at least about 5 mole % of an ester of a linear fatty acid of $C_n$ chain length.

9. The process of claim 1, wherein n=12, 14 or 16.

10. The process of claim 3, wherein n=12, 14 or 16.

11. The process of claim 1, wherein the concentration of metal in the catalyst is about 0.1 to about 90 percent by weight, based on the total weight of the catalyst.

12. The process of claim 1, wherein the feed is a renewable resource obtained from a bio-diesel or green diesel process.

13. The process of claim 1, wherein the linear alkane of $C_n$ chain length, or portion thereof, is fermented with a yeast.

14. The process of claim 13, wherein the yeast is a transformed *Candida maltosa* strain.

15. The process of claim 13, wherein the yeast is a transformed *Pichia pastoris* strain.

16. The process of claim 1, further comprising a step of polymerizing the linear dicarboxylic acid of $C_n$ chain length.

17. The process of claim 1, wherein n=16 or 18.

18. The process of claim 1, wherein the hydrocarbon product has a 13.5:1 ratio of $C_{18}$ to $C_{17}$ alkanes.

* * * * *

SEQUENCE LISTING

```
<160> NUMBER OF SEQ ID NOS: 2

<210> SEQ ID NO 1
<211> LENGTH: 1572
<212> TYPE: DNA
<213> ORGANISM: Candida maltosa

<400> SEQUENCE: 1
atggctatag aacaaattat tgaagaagta cttccttact taactaaatg gtacaccatt        60
ttatttggtg cagctgtcac ttactttta tctatcgctt taagaaataa attttacgaa       120
```

```
tataaattga atgtgaaaa tccagtatac tttgaagatg ctggtttgtt tggtattcca      180
gctttaatcg atatcattaa agttagaaaa gcaggtcaat tagccgacta tactgatact      240
acttttgata aatatccaaa cctctcctct tacatgactg ttgctggtgt tttgaaaatt      300
gtttttactg ttgatccaga aaacatcaaa gctgtcttag ctacccaatt taatgatttc      360
gctttaggtg ccagacatgc tcactttgat ccattgttgg gtgatggtat tttcactttg      420
gatggtgaag gttggaaact tagtagagct atgttgagac cacaatttgc cagagaacaa      480
attgctcatg ttaaagcttt agaaccacat gttcaaatct tggctaaaca aattaaatta      540
aacaagggta aaacttttga cttacaagaa ttattcttca gatttaccgt tgataccgct      600
actgaatttt tgtttggtga atccgtccac agtttgtacg atgaaaaatt gggcattcct      660
gctccaaacg atatcccagg tagagaaaat ttcgctgaag ctttcaacac ttcccaacat      720
tatttagcta ccagaactta cagtcaaatc ttttactggt taactaaccc taaagaattc      780
agagattgta atgctaaagt ccataaatta gctcaatatt tcgttaacac tgctttgaat      840
gccactgaaa aagaagttga agaaaaatct aaaggtggtt acgttttctt gtatgaattg      900
gttaaacaaa ctagagatcc aaaagttttg caagatcaat tattaaacat tatggttgcc      960
ggtagagata ccactgcagg tttattgtct tttgctatgt ttgaattggc cagaaaccca      1020
aagatttgga acaaattgag agaagaagtt gaagttaatt tcggattggg tgacgaagcc      1080
agagtcgacg aaatttcttt tgaaactttg aagaaatgtg aatacttgaa agctgtcttg      1140
aatgaaacct taagaatgta tccttccgtc ccaattaatt tcagaactgc taccagagac      1200
acaacattac caagaggtgg tggtaaagat ggtaactctc ctatctttgt tccaaaaggt      1260
tcttctgttg tttactctgt ttacaaaact cacagattga agcaattcta tggtgaagac      1320
gcttatgaat tcagaccaga aagatggttt gaaccaagta ctagaaaatt gggttgggct      1380
tatcttccat tcaatggtgg tccaagaatt tgtttgggtc agcaatttgc tttgactgaa      1440
gcttcatatg ttattgccag attggcccaa atgtttgaac atttggaatc taaagatgaa      1500
acttacccac caaacaaatg tattcatctt accatgaacc ataacgaagg ggtgtttatt      1560
tctgctaaat ag                                                          1572

<210> SEQ ID NO 2
<211> LENGTH: 1581
<212> TYPE: DNA
<213> ORGANISM: Candida maltosa

<400> SEQUENCE: 2
atgacttccg attcaactat tcacgaatta ttcaatcat acattaccaa atggtatgtc       60
attgtaccac tcgctatcat catctataaa gtattcgatt acttctatgt cttaagttta      120
aggaaaagac ttggagctgc agttccaact aatgaagaaa ccgatggtta tttcgggttc      180
catttacctt tgtttttaat gtcaaaaaag aaagatggta ccatcattga ttttccatt       240 gaacgttacc cagaacttaa acacccagaa acccaacat ttgaattccc aattttttact      300 gtcaaattga tttctactat tgatccgaaa aatatcaaag ctattttagc tacccagttt      360
agtgatttct ccttgggaac tagacatgca cattttgctc ctttaattgg agatggtatt      420
ttcactttgg atggtgctgg ctggaaacat agtgagcca tgttgagacc acaatttgcc      480
agagaacaag ttggtcatgt taaattatta gaaccacacg ttcaagtctt gtttaaacat      540
atcagaaaga ataaaggtag agaatttgat cttcaagaat tatttttcag atttactgtt      600
gattctgcca ctgaattttt gtttggtgaa tccgttgaat cttttacgtga tgcttctatt      660
```

-continued

```
ggtatgactt caaaatctaa agacgttgac ggtattgaag atttcactgg cgcttttaac    720
tattctcaaa actacttggc ttctcgaagc atcatgcaac aattttactg gatcttgaat    780
ggtaaaaaat tcagagaatg taatgctatt gtccataaat ttgctgacca ctatgtccaa    840
aaagccttga atttgactga agctgatttg gaaaaacaag cgggttatgt gtttttgtat    900
gaattggtta aacaaactag agatccacaa gtgttgagag atcaattgtt gaatattttg    960
gttgctggaa gagatacaac tgctggtttg ttgtcgtttg tgtttttcga attggccaga   1020
aatcctgatg ttgttgccaa gttgaaagat gaaattgata ccaagtttgg attaggtgaa   1080
gatgctcgta ttgaagaaat tactttcgaa tctttgaaac aatgtgaata cttgaaggct   1140
gtgctcaatg aatgtttaag attgtatcct tctgttccac aaaatttcag agttgctact   1200
aagaatacta cattaccaag aggtggtggt aaagatggat tgtctccaat attggttaga   1260
aagggacaaa ctgttatgta cagtgtttat gctactcaca gaatggaatc tgtttacggt   1320
aaagatgcaa ccactttcag accagaaaga tggtttgaac cagaaaccag aaaattgggt   1380
tgggcttttg ttccattcaa tggtggtcca agaatctgtt taggtcaaca atttgcttta   1440
actgaagctt cctacgttac agttagatta ctccaagaat ttagtactttt gactctggac   1500 ccaaatcttg aatatccacc aaagaaaatg tcccatttga ccatgtcgct tttcgatggt   1560
acaaacgttc aaatgtatta g                                              1581
```